US008255046B2

(12) United States Patent
Sarkar et al.

(10) Patent No.: US 8,255,046 B2
(45) Date of Patent: Aug. 28, 2012

(54) DETECTING WORSENING HEART FAILURE BASED ON IMPEDANCE MEASUREMENTS

(75) Inventors: Shantanu Sarkar, Roseville, MN (US); Douglas A. Hettrick, Andover, MN (US); Robert W. Stadler, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 848 days.

(21) Appl. No.: 12/184,149

(22) Filed: Jul. 31, 2008

(65) Prior Publication Data

US 2010/0030292 A1 Feb. 4, 2010

(51) Int. Cl.
*A61B 5/05* (2006.01)

(52) U.S. Cl. ........ 600/547; 600/506; 600/508; 600/509; 600/526; 607/17

(58) Field of Classification Search .................. 600/506, 600/508–509, 526, 547; 607/17
See application file for complete search history.

(56) References Cited

U.S. PATENT DOCUMENTS

| | | |
|---|---|---|
| 4,374,382 A | 2/1983 | Markowitz |
| 4,823,797 A | 4/1989 | Heinze et al. |
| 5,107,833 A | 4/1992 | Barsness |
| 5,117,824 A | 6/1992 | Keimel et al. |
| 5,168,871 A | 12/1992 | Grevious |
| 5,271,395 A | 12/1993 | Wahlstrand et al. |
| 5,292,343 A | 3/1994 | Blanchette et al. |
| 5,314,450 A | 5/1994 | Thompson |
| 5,324,315 A | 6/1994 | Grevious |
| 5,354,319 A | 10/1994 | Wyborny et al. |
| 5,383,909 A | 1/1995 | Keimel |
| 5,545,186 A | 8/1996 | Olson et al. |
| 5,755,736 A | 5/1998 | Gillberg et al. |
| 5,836,975 A | 11/1998 | DeGroot |
| 5,876,353 A | 3/1999 | Riff |
| 5,957,861 A | 9/1999 | Combs et al. |
| 6,045,513 A | 4/2000 | Stone et al. |
| 6,102,874 A | 8/2000 | Stone et al. |

(Continued)

FOREIGN PATENT DOCUMENTS

DE 10148440 A1 4/2003

(Continued)

OTHER PUBLICATIONS

International Search Report and Written Opinion from corresponding PCT Application Serial No. PCT/US2008/009336, mailed May 4, 2009 (9 pgs.).

(Continued)

*Primary Examiner* — Rex R Holmes
(74) *Attorney, Agent, or Firm* — Michael C. Soldner

(57) ABSTRACT

Techniques for processing impedance data to provide an early warning for heart failure decompensation are described. An example device may be configured to measure intrathoracic impedance values, and increment an index when a determined impedance is less than a reference impedance. The incrementing may be based on the difference between the reference impedances and the determined impedance. In some examples, the amount of incrementing is reduced based on a variability of the impedances, or increased over time so long as the index remains above a threshold, e.g., zero. In some examples, the manner is which the reference impedances are determined changes over time to, for example, address rapid changes in impedance after device or system implantation. In some examples, the index is compared to a threshold to determine whether to provide an alert. In some examples, two thresholds are used to provide hysteresis.

33 Claims, 14 Drawing Sheets

U.S. PATENT DOCUMENTS

| | | | |
|---|---|---|---|
| 6,104,949 | A | 8/2000 | Crick et al. |
| 6,148,233 | A | 11/2000 | Owen et al. |
| 6,154,674 | A | 11/2000 | Meier |
| 6,221,011 | B1 | 4/2001 | Bardy |
| 6,263,243 | B1 | 7/2001 | Lang |
| 6,277,072 | B1 | 8/2001 | Bardy |
| 6,280,380 | B1 | 8/2001 | Bardy |
| 6,280,409 | B1 | 8/2001 | Stone et al. |
| 6,336,903 | B1 | 1/2002 | Bardy |
| 6,405,085 | B1 | 6/2002 | Graupner et al. |
| 6,449,509 | B1 | 9/2002 | Park et al. |
| 6,459,929 | B1 | 10/2002 | Hopper et al. |
| 6,463,326 | B1 | 10/2002 | Hartley et al. |
| 6,473,640 | B1 | 10/2002 | Erlebacher |
| 6,480,733 | B1 | 11/2002 | Turcott |
| 6,512,949 | B1 | 1/2003 | Combs et al. |
| 6,572,557 | B2 | 6/2003 | Tchou et al. |
| 6,595,927 | B2 | 7/2003 | Pitts-Crick et al. |
| 6,671,549 | B2 | 12/2003 | Van Dam et al. |
| 6,821,249 | B2 | 11/2004 | Casscells, III et al. |
| 6,866,629 | B2 | 3/2005 | Bardy |
| 6,895,275 | B2 | 5/2005 | Markowitz et al. |
| 6,907,288 | B2 | 6/2005 | Daum |
| 6,931,272 | B2 | 8/2005 | Burnes |
| 6,945,934 | B2 | 9/2005 | Bardy |
| 6,960,167 | B2 | 11/2005 | Bardy |
| 7,127,290 | B2 | 10/2006 | Girouard et al. |
| 7,177,681 | B2 | 2/2007 | Zhu et al. |
| 7,184,821 | B2 | 2/2007 | Belalcazar et al. |
| 7,248,916 | B2 | 7/2007 | Bardy |
| 7,272,442 | B2 | 9/2007 | Freeberg |
| 7,308,309 | B1 | 12/2007 | Koh |
| 7,310,551 | B1 | 12/2007 | Koh et al. |
| 7,313,434 | B2 | 12/2007 | Belalcazar et al. |
| 7,340,296 | B2 | 3/2008 | Stahmann et al. |
| 7,387,610 | B2 | 6/2008 | Stahmann et al. |
| 7,389,143 | B2 | 6/2008 | Hopper et al. |
| 2001/0011153 | A1 | 8/2001 | Bardy |
| 2001/0021801 | A1 | 9/2001 | Bardy |
| 2001/0039504 | A1 | 11/2001 | Lindberg et al. |
| 2002/0026104 | A1 | 2/2002 | Bardy |
| 2003/0028221 | A1 | 2/2003 | Zhu et al. |
| 2003/0055461 | A1 | 3/2003 | Girouard et al. |
| 2003/0125611 | A1 | 7/2003 | Bardy |
| 2003/0149367 | A1 | 8/2003 | Kroll et al. |
| 2003/0220580 | A1* | 11/2003 | Alt ................ 600/547 |
| 2004/0102712 | A1 | 5/2004 | Belalcazar et al. |
| 2004/0122484 | A1 | 6/2004 | Hatlestad et al. |
| 2004/0172080 | A1 | 9/2004 | Stadler et al. |
| 2005/0124908 | A1 | 6/2005 | Belalcazar et al. |
| 2006/0020295 | A1 | 1/2006 | Brockway et al. |
| 2006/0293609 | A1* | 12/2006 | Stahmann et al. ......... 600/547 |
| 2007/0142732 | A1 | 6/2007 | Brockway et al. |
| 2007/0156061 | A1 | 7/2007 | Hess |
| 2008/0024293 | A1 | 1/2008 | Stylos |
| 2008/0027349 | A1* | 1/2008 | Stylos ................ 600/547 |
| 2008/0161657 | A1 | 7/2008 | Bullens et al. |
| 2010/0030292 | A1 | 2/2010 | Sarkar et al. |
| 2010/0030293 | A1 | 2/2010 | Sarkar et al. |
| 2010/0114241 | A1 | 5/2010 | Donofrio et al. |
| 2010/0198097 | A1 | 8/2010 | Sowelam |

FOREIGN PATENT DOCUMENTS

| | | |
|---|---|---|
| EP | 1997427 A1 | 4/2008 |
| WO | 9833554 A1 | 8/1998 |
| WO | 0064336 A1 | 11/2000 |
| WO | 0132260 A1 | 5/2001 |
| WO | 2006/070124 A1 | 7/2006 |
| WO | 2006081432 A1 | 8/2006 |
| WO | 2007/079354 A2 | 7/2007 |

OTHER PUBLICATIONS

Adamson et al, "Continuous Autonomic Assessment in Patients with Symptomatic Heart Failure . . . " Circulation Journal of American Heart Association, pp. 2389-2394, 110:16, Lippincott Williams & Wilkins, Baltimore MD, 2004.

Lusignan, et al. "Compliance and Effectiveness of 1 Year's Home Telemonitoring. The Report of a Pilot Study . . . " European Journal of Heart Failure, 3:723-730, 2001.

Baer, et al. "Electronic Home Monitoring of Congestive Heart Failure Patients: Design and Feasibility", Congestive Heart Failure, 5:105-113, 1999.

Wuerz & Meador, "Effects of Prehospital Medications on Mortality and Length of Stay in Congestive Heart Failure", Annals of Emergency Medicine 21:6 pp. 669-674, Jun. 1992.

Berman et al. "Transthoracic Electrical Impedance as a Guide to Intravascular Overload", Archives Surgery, 102, pp. 61-62 Jan. 1971.

U.S. Appl. No. 12/112,765, filed Apr. 30, 2008 by Todd M. Zielinski et al.

International Search Report and Written Opinion from PCT Application Serial No. PCT/US2010/054539 dated Feb. 4, 2011 (11 pages).

International Preliminary Report on Patentability from international application No. PCT/US2008/009336, dated Feb. 10, 2011, 7 pp.

Office Action from U.S. Appl. No. 12/184,003, dated Jun. 28, 2011, 11 pp.

Response to Office Action dated Jun. 28, 2011, from U.S. Appl. No. 12/184,003, filed Sep. 28, 2011, 15 pp.

Office Action from U.S. Appl. No. 12/184,003, dated Dec. 21, 2011, 11 pp.

Office Action from U.S. Appl. No. 12/363,264, dated Nov. 30, 2011, 5 pp.

Response to Office Action dated Dec. 21, 2011, from U.S. Appl. No. 12/184,003, filed Feb. 21, 2012, 7 pp.

Response to Office Action dated Nov. 30, 2011, from U.S. Appl. No. 12/363,264, filed Feb. 29, 2012, 9 pp.

Office Action from U.S. Appl. No. 12/363,264, dated May 9, 2012, 9 pages.

* cited by examiner

DETECTING WORSENING HEART FAILURE BASED ON IMPEDANCE MEASUREMENTS

TECHNICAL FIELD

The invention relates to medical devices and, more particularly, medical devices for detecting or monitoring heart failure.

BACKGROUND

A variety of medical devices have been used or proposed for use to deliver a therapy to and/or monitor a physiological condition of patients. As examples, such medical devices may deliver therapy and/or monitor conditions associated with the heart, muscle, nerve, brain, stomach or other organs or tissue. Medical devices that deliver therapy include medical devices that deliver one or both of electrical stimulation or a therapeutic agent to the patient. Some medical devices are implantable medical devices (IMDs) that are implanted within the patient.

Some medical devices have been used or proposed for use to monitor heart failure or to detect heart failure events. Typically, such medical devices have been implantable and, in many cases, have been cardiac pacemakers, cardioverters and/or defibrillators with added heart failure monitoring functionality. In some cases, such medical devices have monitored heart failure by monitoring intrathoracic impedance, which may provide a good indication of the level of edema in patients. While edema is a sign of many other conditions it is also a sign of worsening heart failure. Worsening heart failure may result in cardiac chamber dilation, increased pulmonary blood volume, and fluid retention in the lungs—all of which contribute to a decrease in intrathoracic impedance.

Generally, the first indication that a physician would have of the occurrence of edema in a patient is not until it becomes a physical manifestation with swelling or breathing difficulties so overwhelming as to be noticed by the patient who then proceeds to be examined by a physician. This is undesirable since hospitalization at such a time would likely be required for a cardiac heart failure patient. Accordingly, medical devices have been used to monitor impedance in patients and provide an alert to the patient to seek medical treatment prior to the onset of edema that requires hospitalization.

SUMMARY

This disclosure describes techniques for providing an early warning for heart failure decompensation based on impedance measurements of tissue in a body of a patient. Intrathoracic impedance is an example of an impedance which may be monitored to detect worsening heart failure, e.g., based on edema. The techniques may be implemented by an implantable medical device (IMD), such as a pacemaker, cardioverter, defibrillator, or pacemaker-cardioverter-defibrillator, coupled to a plurality of lead-borne electrodes for measuring the impedances.

A device, e.g., an IMD, compares the measured impedances to reference impedances to accumulate evidence of decreasing impedance and, therefore, worsening heart failure. This evidence is referred to as a fluid index, and may reflect a level of pulmonary edema, increased ventricular filling pressures or other morbidities associated with worsening heart failure experienced by a patient. The fluid index is one example of an index that indicates worsening heart failure. Other examples include indices or metrics of increased ventricular filling pressures or other morbidities associated with worsening heart failure experienced by a patient. In general, any parameter that indicates worsening heart failure may be monitored according to the techniques described herein, and an index that indicates worsening heart failure may be any index that is incremented to indicate a trend in the parameter that reflects worsening heart failure.

The reference impedance may be determined based on the previously measured impedances. In some examples, the device increments the fluid index based on the differences between measured impedances and reference impedances, and may increment the fluid index in this manner so long as the measured impedances are less than their respective reference impedances. The resultant fluid index may be compared to one or more thresholds to determine whether or not an alarm indicating worsening heart failure should be active. The alarm may be communicated directly to the patient or to the clinician through a variety of methods that have been previously described including audible tones, handheld devices and automatic telemetry to computerized communication network.

Various techniques are used to enable the fluid index to accurately represent changes in patient condition over time, and the alarm condition to better correspond to a clinically significant worsening of patient condition. In some examples, the techniques involve varying a parameter that affects a slope of the index over time, to address time-dependent factors or other factors that may affect the accuracy of the fluid index.

In some examples, the amount of incrementing is reduced based on a variability of the measured impedances. Accumulating the fluid index less in the presence of high variability may facilitate accuracy of the fluid index by lessening accumulation during periods of impedance instability that are not directly associated with worsening heart failure. Increasing the accumulation over time may allow consistently decreasing impedances to more quickly result in an alarm condition.

In some examples, the manner is which the reference impedances are determined changes over time. In particular, amounts by which the reference impedance may be incremented or decremented may be relatively high after implantation, and may decrease over time. In this manner, the reference impedance may be able to track rapid changes, typically increases in impedance that are commonly observed after implantation, or after surgical modification of the implanted system, such as lead change/revision or device change.

In some examples, a device adaptively calculates the fluid index over time by accumulating the fluid index based on a finite number of previous comparisons between measured impedances and reference impedances, e.g., over a finite period of time, such as the last X days. For example, a device may sum a finite number of differences between measured and reference impedances, which may be stored in a first-in-first-out (FIFO) buffer of finite size. The finite number of comparisons may act as a sliding window with respect to previous comparisons. By limiting the number of comparisons used to determine the fluid index, accumulation of the fluid index due to clinically insignificant DC impedance shifts and temporary impedance deviations due to, for example, poor adherence to medication regimens or diet restrictions is limited. Alerting in response to such relatively less significant events is also limited. Moreover, limiting the accumulation of the fluid index in this manner may limit alerting to be in response to more recent events, e.g., to avoid alerting due to past compliance issues which may have been resolved.

In some examples, the fluid index is compared to two thresholds to provide hysteresis in the alert decision. An alert is generated when the fluid index crosses a first, higher threshold. The alert is ended when the fluid index subsequently crosses a second, lower threshold. By generating alerts in this manner, a device may generate fewer "sporadic" alerts that may be misinterpreted by the patient or a clinician when the fluid index value fluctuates near the higher, alert threshold value.

In one example, the disclosure provides a method comprising periodically determining an impedance of a patient based on measured impedances, comparing each of the determined impedances to a respective reference impedance, wherein the respective reference impedance for each of the determined impedances is determined based on a plurality of previously determined impedances; modifying an index over time based on the comparisons between the determined impedances and the reference impedances, comparing the index to at least one threshold, determining whether to provide an alert based on the comparison of the index to the at least one threshold, and varying at least one other parameter over time that, in addition to the determined and reference impedances, affects a slope of the index.

In another example, the disclosure provides a method comprising periodically determining an impedance of a patient based on a plurality of measured impedances, comparing each of the determined impedances to a respective reference impedance, wherein the respective reference impedance for each of the determined impedances is determined based on a plurality of previously determined impedances, determining an index based on the previous X or fewer comparisons, wherein X is a predetermined constant value, comparing the index to at least one threshold, and determining whether to provide an alert based on the comparison of the index to the at least one threshold.

In another example, the disclosure provides a method comprising periodically determining an impedance of a patient based on a plurality of measured impedances, comparing each of the determined impedances to a respective reference impedance, wherein the respective reference impedance for each of the determined impedances is determined based on a plurality of previously determined impedances, modifying an index over time based on the comparisons between the determined impedances and the reference impedances, comparing the index to a plurality of thresholds, and determining whether to provide an alert based on the comparison of the index to the plurality of thresholds.

In another example, the disclosure provides a system comprising a plurality of electrodes, a medical device coupled to the electrodes that periodically measures an impedance of the patient and a processor that periodically determines an impedance value based on a plurality of the measured impedances, compares each of the determined impedance values to a respective reference impedance, wherein the respective reference impedance for each of the determined impedance values is determined based on a plurality of previously determined impedance values, modifies an index over time based on the comparisons between the determined impedance values and the reference impedances, compares the index to at least one threshold, determines whether to provide an alert based on the comparison of the index to the at least one threshold, and varies at least one other parameter over time that, in addition to the determined impedance values and reference impedances, affects a slope of the index.

In another example, the disclosure provides a system comprising a plurality of electrodes, a medical device coupled to the electrodes that periodically measures an impedance of the patient and a processor that periodically determines an impedance value based on a plurality of the measured impedances, compares each of the determined impedance values to a respective reference impedance, wherein the respective reference impedance for each of the determined impedance values is determined based on a plurality of previously determined impedance values, determines an index based on the previous X or fewer comparisons, wherein X is a predetermined constant value, compares the index to at least one threshold, and determines whether to provide an alert based on the comparison of the index to the at least one threshold.

In another example, the disclosure provides a system comprising a plurality of electrodes, a medical device coupled to the electrodes that periodically measures an impedance of the patient and a processor that periodically determines an impedance value based on a plurality of the measured impedances, compares each of the determined impedance values to a respective reference impedance, wherein the respective reference impedance for each of the determined impedance values is determined based on a plurality of previously determined impedance values, modifies an index over time based on the comparisons between the determined impedance values and the reference impedances, compares the index to a plurality of thresholds, and determines whether to provide an alert based on the comparison of the index to the plurality of thresholds.

In another example, the disclosure provides a system comprising means for periodically determining an impedance of a patient based on a plurality of measured impedances; means for comparing each of the determined impedances to a respective reference impedance, wherein the respective reference impedance for each of the determined impedances is determined based on a plurality of previous measured impedances; means for modifying an index over time based on the comparisons between the determined impedances and the reference impedances; means for comparing the index to at least one threshold; means for determining whether to provide an alert based on the comparison of the index to the at least one threshold; and means for varying at least one other parameter over time that, in addition to the determined and reference impedances, affects a slope of the index.

In another example, the disclosure provides a system comprising means for periodically determining an impedance of a patient based on a plurality of measured impedances; means for comparing each of the determined impedances to a respective reference impedance, wherein the respective reference impedance for each of the determined impedances is determined based on a plurality of previously determined impedances; means for determining an index based on the previous X or fewer comparisons, wherein X is a predetermined constant value; means for comparing the index to at least one threshold; and means for determining whether to provide an alert based on the comparison of the index to the at least one threshold.

In another example, the disclosure provides a system comprising means for periodically determining an impedance of a patient based on a plurality of measured impedances; means for comparing each of the determined impedances to a respective reference impedance, wherein the respective reference impedance for each of the determined impedances is determined based on a plurality of previously determined impedances; means for modifying an index over time based on the comparisons between the determined impedances and the reference impedances; means for comparing the index to a plurality of thresholds; and means for determining whether to provide an alert based on the comparison of the index to the at least one threshold.

The disclosure also provides means for performing any of the methods described herein, as well as computer-readable media comprising instructions that cause a programmable processor to perform any of the methods described herein.

The details of one or more examples are set forth in the accompanying drawings and the description below. Other features, objects, and advantages of the disclosure will be apparent from the description and drawings, and from the claims.

DETAILED DESCRIPTION

Figure 1:
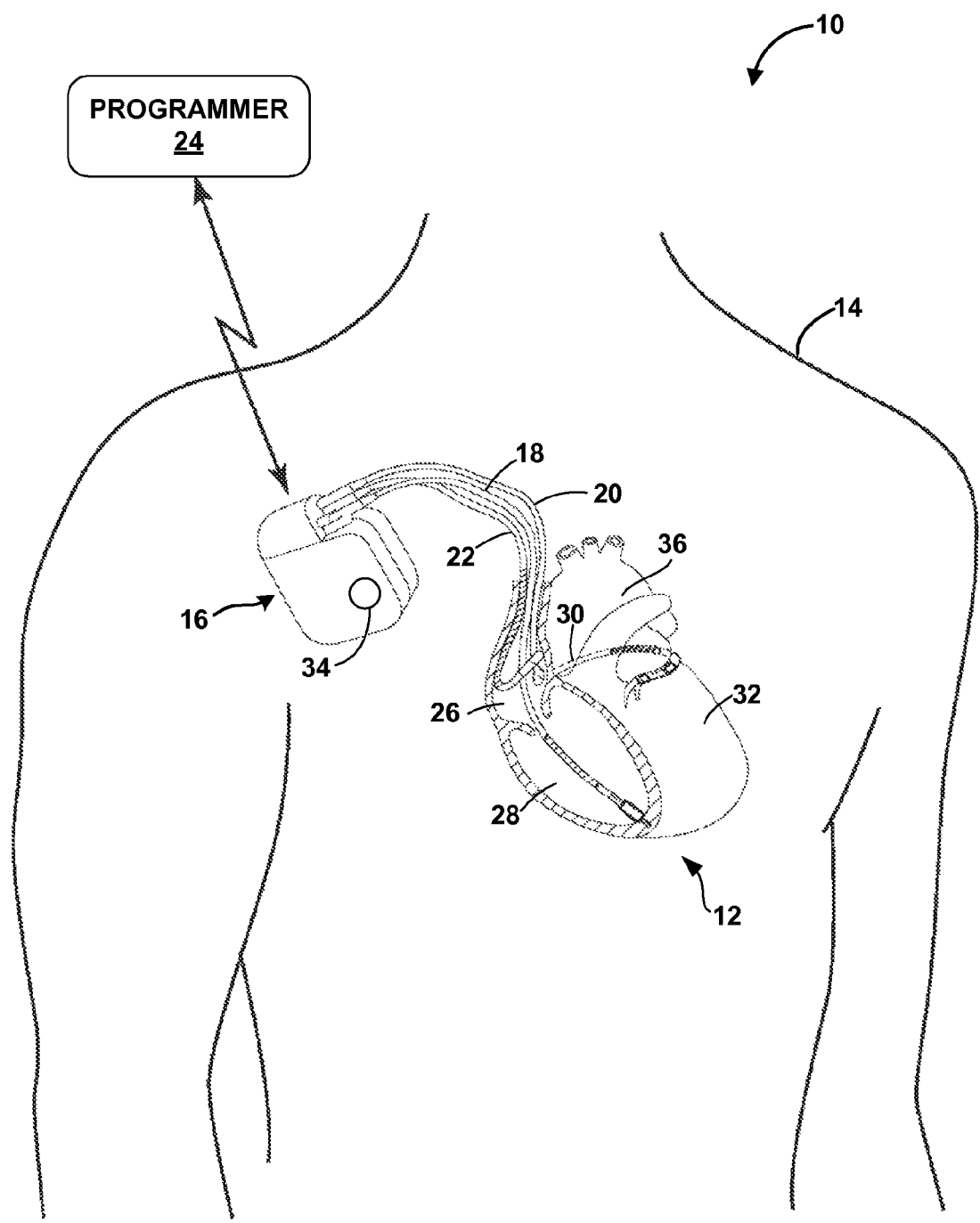
FIG. 1 is a conceptual diagram illustrating an example system that measures thransthoracic impedance to provide an early warning for heart failure decompensation.

FIG. 1 is a conceptual diagram illustrating an example system 10 that may be used to measure intrathoracic impedance to provide to patient 14 or other users an early warning for the onset of a heart failure decompensation event. Patient 14 ordinarily, but not necessarily, will be a human. System 10 includes implantable medical device (IMD) 16, which is coupled to leads 18, 20, and 22, electrode 34 located on the can of device 16, and programmer 24.

In some examples, IMD 16 may be a purely diagnostic device that measures intrathoracic impedance values of patient 14. In other examples, IMD 16 may additionally operate as a therapy delivery device to deliver electrical signals to heart 12, such as an implantable pacemaker, a cardioverter, and/or defibrillator, a drug delivery device that delivers therapeutic substances to patient 14 via one or more catheters, or as a combination therapy device that delivers both electrical signals and therapeutic substances. Moreover, IMD 16 is not limited to devices implanted as shown in FIG. 1. As an example, IMD 16 may be implanted subcutaneously in patient 14. Furthermore, in some examples an external medical device may monitor intrathoracic impedance according to the techniques described herein. An external medical device may be coupled to external electrodes, or to implanted electrodes via percutaneous leads.

In the example shown in FIG. 1, leads 18, 20, and 22 extend into the heart 12 of patient 14. Right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12. Other configurations, i.e., number and position of leads, are possible.

Intrathoracic impedance may be measured by delivering a signal through an electrical path between electrodes (not shown in FIG. 1) located on one or more of leads 18, 20, and 22 and can electrode 34. In some examples, the can of IMD 16 may be used as an electrode in combination with electrodes located on leads 18, 20, and 22. For example, system 10 may measure intrathoracic impedance by creating an electrical path between RV lead 18 and electrode 34. In additional examples, system 10 may include an additional lead or lead segment having one or more electrodes positioned subcutaneously or within the chest cavity for measuring intrathoracic impedance.

In examples in which IMD 16 operates as a pacemaker, a cardioverter, and/or defibrillator, IMD 16 may sense electrical signals attendant to the depolarization and repolarization of heart 12 via electrodes coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22, as well as housing electrode 34. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques known in the art.

In some examples, programmer 24 may be a handheld computing device, computer workstation, or networked computing device. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some examples, a display of programmer 24 may include a touch screen display, and a user may interact with programmer 24 via the display. It should be noted that the user may also interact with programmer 24 remotely via a networked computing device.

A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16. The information may relate to intrathoracic impedance, trends therein over time, or other associated data as described herein. In some examples, the user may also use programmer 24 to retrieve information regarding the rhythm of heart 12, trends therein over time, or arrhythmic episodes. In other example examples, the user may use programmer 24 to retrieve information from IMD 16 regarding other sensed physiological parameters of patient 14, such as intracardiac or intravascular pressure, activity, posture, or respiration.

The user may use programmer 24 to program impedance measurement parameters such as to select electrodes used to measure intrathoracic impedance, and select waveforms for measuring intrathoracic impedance. Programmer 24 may also be used to program a therapy progression, select electrodes to deliver defibrillation pulses, select waveforms for the defibrillation pulse, or select or configure a fibrillation detection algorithm for IMD 16. The user may also use programmer 24 to program aspects of other therapies provided by IMD 16, such as cardioversion or pacing therapies. In some examples, the user may activate certain features of IMD 16 by entering a single command via programmer 24, such as depression of a single key or combination of keys of a keypad or a single point-and-select action with a pointing device.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

System 10 measures intrathoracic impedance of patient 14 and processes impedance data to accumulate evidence of decreasing impedance. The accumulated evidence is referred to as a fluid index, and may be determined as function of the difference between measured impedance values and reference impedance values. System 10 provides an alert to patient 14 and/or other users when the fluid index indicates the onset of a heart failure decompensation event. The process for determining when to alert patient 14 involves comparing the fluid index to one or more threshold values and is described in greater detail below. The alert may be an audible alert generated by IMD 16 and/or programmer 24, a visual alert generated by programmer 24, such as a text prompt or flashing buttons or screen, or a tactile alert generated by IMD 16 and/or programmer 24 such as a vibration or vibrational pattern. Furthermore, the alert may be provided to other devices, e.g., via a network.

At least three morphologies of impedance decreases have been found to occur in patients. The first form of impedance decrease represents a gradual and consistent decrease in impedance over an extended period of time. The duration of this type of impedance decrease is longer than a month. This impedance decrease is strongly associated with worsening cardiac heart failure.

The second form of impedance decrease is characterized by a sudden drop in impedance followed by a trend of increasing impedance back towards the baseline impedance. This type of event may result from changes in patient compliance behaviors, such as medication or dietary indiscretion, or result from acute decompensation that may lead to medical intervention. Thus, some of these crossing may be critical while others may be less critical.

The third form of impedance decrease results from small DC shifts in impedance. Because these small shifts may occur several times, they may eventually lead to threshold crossings if the fluid index is accumulated over a long period of time. For example, a sustained shift in impedance of even two or three ohms may result in a crossing if sustained for a sufficient period of time. The standard deviation of day to day variation in impedance has been observed to be on the order of three ohms. Thus, this class of decrease in impedance is not considered clinically critical but can lead to false alerts if the processing technique is not properly designed.

Moreover, the implant procedure causes another distinct feature in the impedance trend of the patient. This feature is that the daily impedance increases over several months following the implant procedure and that the rate of increase over time slows as the daily impedance plateaus toward a baseline value. This phenomenon is believed to be due to the drying out of the device pocket and encapsulation of the lead post implant. In other words, because the device pocket is filled with fluid immediately following the implant procedure the measured impedance is relatively low because the resistance of the fluid is less than the resistance of body tissue. However, as the fluid dissipates over time the resistance increases and the rate at which the fluid dissipates decreases as time progresses. This can result in the daily impedance tending to be higher than the reference impedance during the first few months following the implant procedure. As a result, the fluid index may be less sensitive to actual decreases in the daily impedance. This is undesirable.

System 10 addresses these issues through adaptive processing techniques. The adaptive processing techniques may limit fluid index threshold crossings for small amplitude shifts in the measured impedance, limit fluid index increases while the daily impedance is recovering or increasing toward a baseline value, and allow the rate of change of the reference impedance value to change over time.

In one example, system 10 may calculate the fluid index based on the variability of measured impedance values. In particular, system 10 may determine the fluid index in a way that mitigates the accumulation of decreasing impedance when there is a greater variability on a day to day basis. System 10 may also give greater weight to the variability according to the time that has elapsed since implant or a prior detected event.

In an additional example, system 10 may calculate the fluid index by accumulating the fluid index over a finite period of time using a finite number of differences between measured and reference impedances. That is, system 10 may use a sliding window technique to calculate the fluid index. This technique may avoid accumulating to the fluid index to an alert condition as the baseline impedance tries to "catch-up" to a baseline shift in the measured impedances.

In a further example, system 10 may calculate the fluid index over time by factoring in a time dependent value. In this way the time dependent value may be used to increase the value of the fluid index after the measured impedances have been below the reference impedance for a threshold duration, e.g., a month, which may indicate a clinically significant worsening of patient condition.

In another example, system 10 may adaptively calculate reference impedance values over time. In particular, system 10 may calculate reference impedance in a manner that accommodates the different rates of change in impedance over time. In other words, reference impedance values may be calculated differently during different periods of time. For example, the reference impedance values may be calculated to allow for a greater change in reference impedance during day 0 to day 60 following the implant or system modification than during days 61 to 100. The reference impedance values may then be calculated to allow for a lesser change in value for the days extending past day 100 than for the previous time period.

In another example, system 10 provides an alert to patient 14 based on a comparison of the fluid index to more than one threshold value. Specifically, system 10 begins comparing the fluid index to a first threshold value. When the fluid index value is greater than the first threshold value, system 10 provides an alert to patient 14. After each subsequent calculation of the fluid index, the fluid index is compared to a second threshold value. The second threshold value is less than the first threshold value so that the resulting comparison will continue to cause system 10 to generate an alert when the fluid index is approximately equal to the threshold value. By using the second threshold value, system 10 provides hysteresis for the alert, and continues to generate alerts as long as the fluid index remains within a predetermined margin of the first threshold. Without the second threshold value, the fluid index would reset when it drops below the first threshold. This could cause "sporadic" alerts that may be misinterpreted as errors, rather than interpreted as an indication that the fluid index is remaining near the value that indicates the onset of a heart failure decompensation event.

Figure 2:
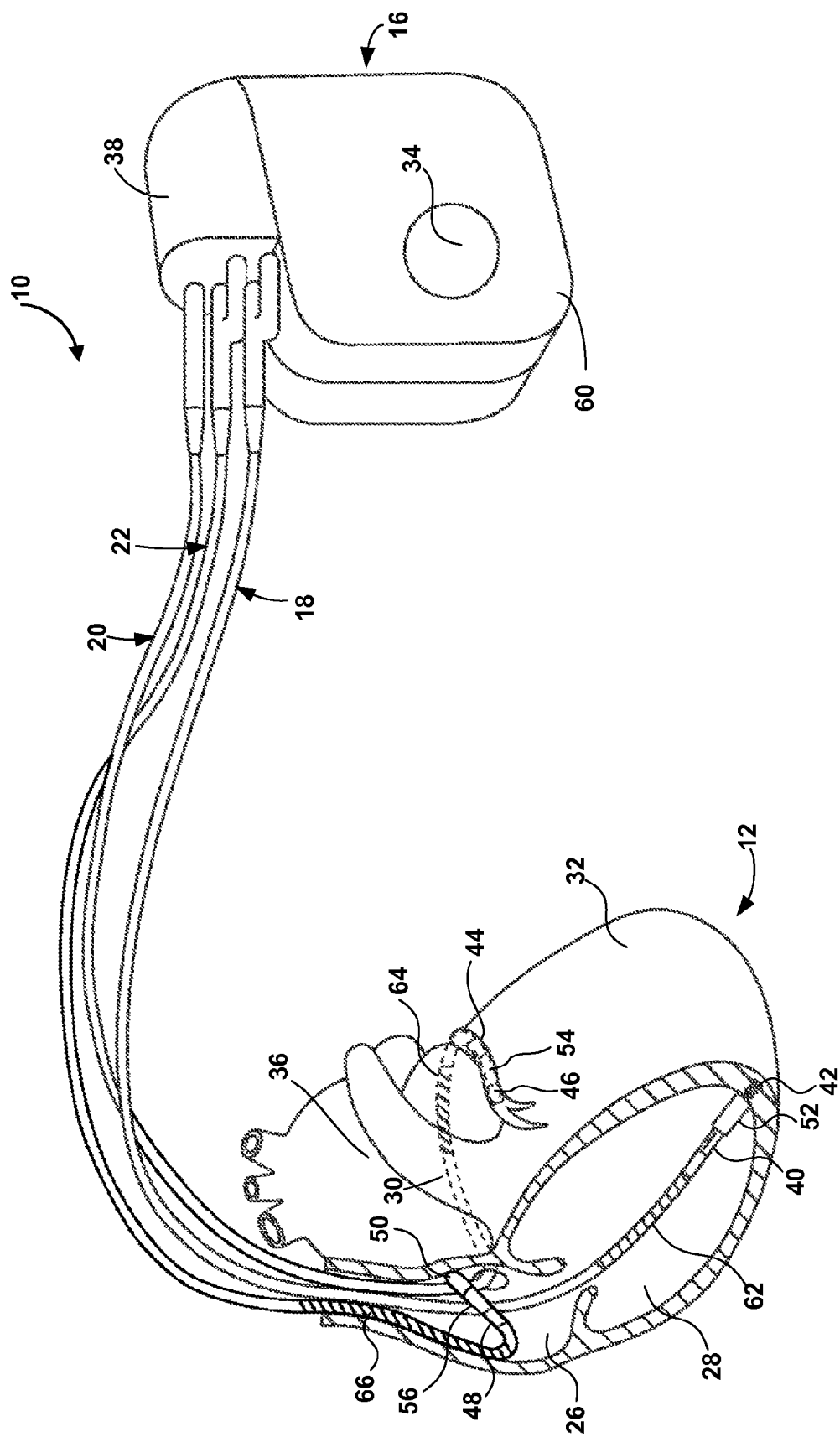
FIG. 2 is a conceptual diagram illustrating the implantable medical device (IMD) and leads of the system shown in FIG. 1 in greater detail.

FIG. 2 is a conceptual diagram illustrating IMD 16, leads 18, 20, and 22, and electrode 34 of therapy system 10 in greater detail. Leads 18, 20, 22 may be electrically coupled to a stimulation generator and a sensing module of IMD 16 via connector block 38. In some examples, proximal ends of leads 18, 20, 22 may include electrical contacts that electrically couple to respective electrical contacts within connector block 38. In addition, in some examples, leads 18, 20, 22 may be mechanically coupled to connector block 38 with the aid of set screws, connection pins, or another suitable mechanical coupling mechanism.

Each of the leads 18, 20, 22 includes an elongated insulative lead body, which may carry a number of concentric coiled conductors separated from one another by tubular insulative sheaths. In some cases, each of the leads 18, 20, 22 may include cable conductors. Bipolar electrodes 40 and 42 are located adjacent to a distal end of lead 18. In addition, bipolar electrodes 44 and 46 are located adjacent to a distal end of lead 20 and bipolar electrodes 48 and 50 are located adjacent to a distal end of lead 22.

Electrodes 40, 44 and 48 may take the form of ring electrodes, and electrodes 42, 46 and 50 may take the form of extendable helix tip electrodes mounted retractably within insulative electrode heads 52, 54 and 56, respectively. In other embodiments, one or more of electrodes 42, 46 and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64 and 66 may be electrically coupled to a respective one of the coiled conductors within the lead body of its associated lead 18, 20, 22, and thereby coupled to respective ones of the electrical contacts on the proximal end of leads 18, 20 and 22.

As discussed above, IMD 16 includes one or more housing electrodes, such as housing electrode 34, which may be formed integrally with an outer surface of hermetically-sealed housing 60 of IMD 16 or otherwise coupled to housing 60. In some examples, housing electrode 34 is defined by an uninsulated portion of an outward facing portion of housing 60 of IMD 16. Other division between insulated and uninsulated portions of housing 60 may be employed to define two or more housing electrodes. In some examples, housing electrode 34 comprises substantially all of housing 60. As described in further detail with reference to FIG. 3, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 34, 40, 42, 44, 46, 48, 50, 62, 64 and 66. The electrical signals are conducted to IMD 16 from the electrodes via the respective leads 18, 20, 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 34. Additionally, any of the electrodes 40, 42, 44, 46, 48, 50, 62, 64 and 66 may be used in combination with housing electrode 34 to sense intrathoracic impedance of patient 14.

IMD 16 may process the sensed electrical signals to monitor secondary diagnostic parameters such as atrial fibrillation (AF), heart rate during AF, ventricular fibrillation (VF), heart rate during VF, atrial tachyarrhythmia (AT), heart rate during AT, ventricular tachyarrhythmia (VT), heart rate during VT, activity level, heart rate variability, and night heart rate. IMD 16 may also process the intrathoracic impedance sensed by electrodes 34, 40, 42, 44, 46, 48, 50, 62, 64, or 66 as a primary diagnostic parameter to modify a fluid index, as well as to detect respiratory rate, depth, or pattern, which may be secondary diagnostic parameters.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 34 in a unipolar configuration. Furthermore, IMD 16 may deliver cardioversion or defibrillation pulses to heart 12 via any combination of elongated electrodes 62, 64, 66, and housing electrode 34. Electrodes 34, 62, 64, 66 may also be used to deliver cardioversion pulses, e.g., a responsive therapeutic shock, to heart 12. Electrodes 62, 64, 66 may be fabricated from any suitable electrically conductive material, such as, but not limited to, platinum, platinum alloy or other materials known to be usable in implantable defibrillation electrodes.

The configuration of system 10 illustrated in FIGS. 1 and 2 is merely one example. In other examples in which system 10 operates as a therapy system, system 10 may include epicardial leads and/or patch electrodes instead of or in addition to the transvenous leads 18, 20, 22 illustrated in FIG. 1. Further, IMD 16 need not be implanted within patient 14 as shown in FIG. 1. For example, IMD 16 may be implanted subcutaneously in patient 14 and measure intrathoracic impedance via leads implanted subcutaneously in the chest of patient 14 or located on the chest of patient 14. In examples in which IMD 16 is not implanted in patient 14, IMD 16 may measure intrathoracic impedance and deliver defibrillation pulses and other therapies to heart 12 via percutaneous leads that extend through the skin of patient 14 to a variety of positions within or outside of heart 12.

In addition, in other examples, system 10 may include any suitable number of leads coupled to IMD 16, and each of the leads may extend to any location within or proximate to heart 12 or in the chest of patient 14. For example, other examples therapy systems may include three transvenous leads and an additional lead located within or proximate to left atrium 36. As other examples, a therapy system may include a single lead that extends from IMD 16 into right atrium 26 or right ventricle 28, or two leads that extend into a respective one of the right ventricle 28 and right atrium 26.

Figure 3:
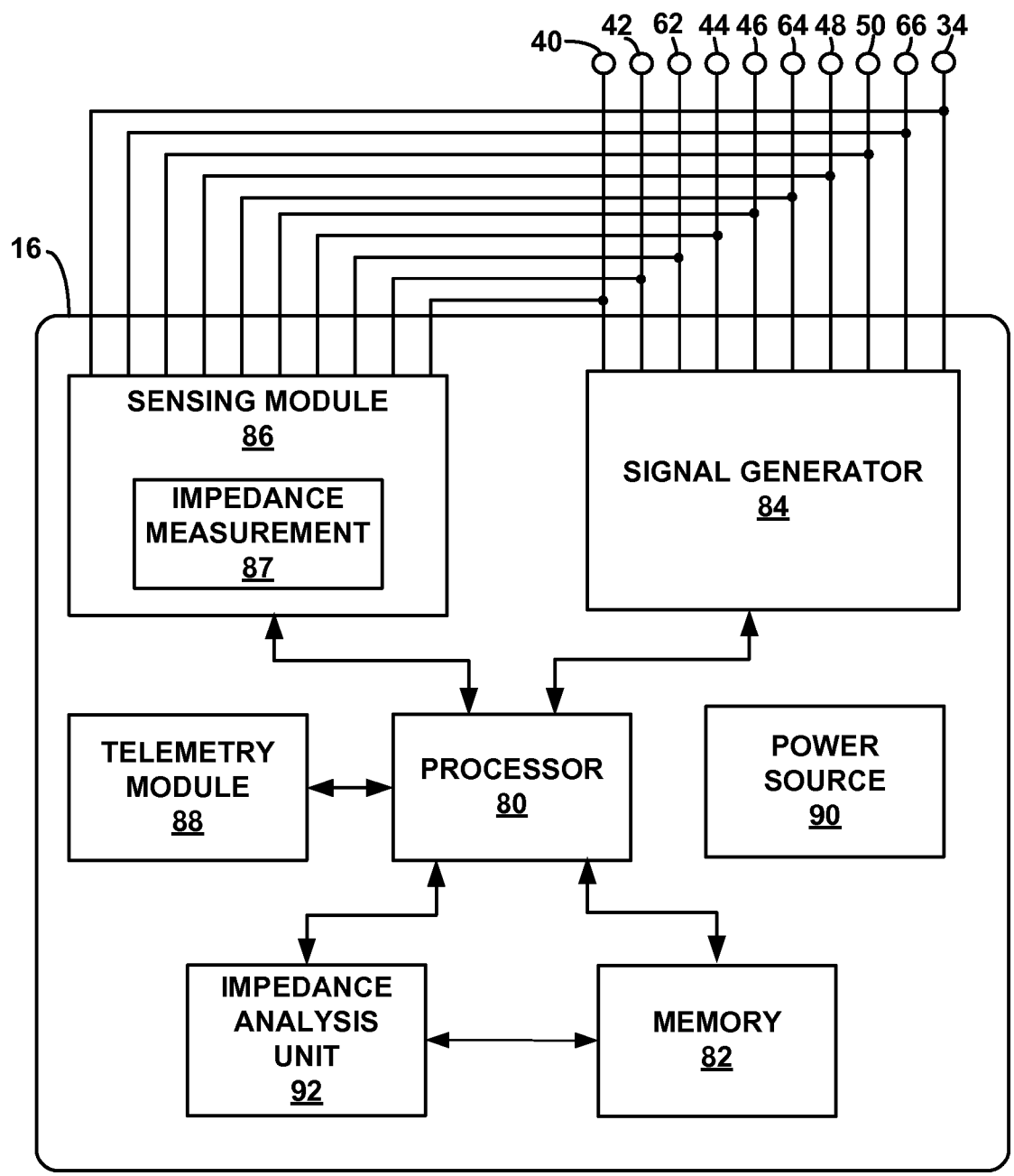
FIG. 3 is a functional block illustrating an example configuration of the IMD shown in FIG. 1.

FIG. 3 is a functional block diagram of one example of IMD 16, which includes processor 80, memory 82, stimulation generator 84, sensing module 86, telemetry module 88, power source 90, and impedance analysis unit 92. Processor 80 may comprise one or more processors. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 controls signal generator 84 to deliver stimulation therapy to heart 12 based on a selected one or more of therapy programs, which may be stored in memory 82. Specifically, processor 80 may control signal generator 84 to deliver electrical pulses with the amplitudes, pulse widths, frequency, or electrode polarities specified by the selected one or more therapy programs.

Signal generator 84 is electrically coupled to electrodes 34, 40, 42, 44, 46, 48, 50, 62, 64, and 66, e.g., via conductors of the respective lead 18, 20, 22, or, in the case of housing electrode 34, via an electrical conductor disposed within housing 60 of IMD 16. A switch matrix may also be provided to connect signal generator 84 to one or more of electrodes 34, 40, 42, 44, 46, 48, 50, 62, 64, and 66. Signal generator 84 is configured to generate and deliver electrical stimulation therapy to heart 12.

For example, signal generator 84 may deliver defibrillation shocks to heart 12 via at least two of electrodes 34, 62, 64, 66. Signal generator 84 may also deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator 84 may deliver one or more of these types of stimulation in the form of other signals, such as sine waves, square waves, or other substantially continuous time signals.

Signal generator 84 may include a switch module, and processor 80 may use the switch module to select, e.g., via a data/address bus, which of the available electrodes are used to deliver defibrillation pulses or pacing pulses. The switch module may include a switch array, switch matrix, multiplexer, transistor array, microelectromechanical switches, or any other type of switching device suitable to selectively couple stimulation energy to selected electrodes.

Electrical sensing module 86 monitors signals from at least one of electrodes 34, 40, 42, 44, 46, 48, 50, 62, 64 or 66 in order to monitor electrical activity of heart 12. Sensing module 86 may also include a switch module to select which of the available electrodes are used to sense the heart activity. In some examples, processor 80 may select the electrodes that function as sense electrodes via the switch module within sensing module 86, e.g., by providing signals via a data/address bus. In some examples, sensing module 86 includes one or more sensing channels, each of which may comprise an amplifier. In response to the signals from processor 80, the switch module within sensing module 86 may couple the outputs from the selected electrodes to one of the sensing channels.

In some examples, one channel of sensing module 86 may include an R-wave amplifier that receives signals from electrodes 40 and 42, which are used for pacing and sensing in right ventricle 28 of heart 12. Another channel may include another R-wave amplifier that receives signals from electrodes 44 and 46, which are used for pacing and sensing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, one channel of sensing module 86 may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 84 may be selectively coupled to housing electrode 34, or elongated electrodes 62, 64, or 66, with or instead of one or more of electrodes 40, 42, 44, 46, 48 or 50, e.g., for unipolar sensing of R-waves or P-waves in any of chambers 26, 28, 36, or 32 of heart 12.

In some examples, sensing module 84 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 82 as an electrogram (EGM). In some examples, the storage of such EGMs in memory 82 may be under the control of a direct memory access circuit. Processor 80 may employ digital signal analysis techniques to characterize the digitized signals stored in memory 82 to detect and classify the patient's heart rhythm from the electrical signals. Processor 80 may detect and classify the patient's heart rhythm by employing any of the numerous signal processing methodologies known in the art.

If IMD 16 is configured to generate and deliver pacing pulses to heart 12, processor 80 may include pacer timing and control module, which may be embodied as hardware, firmware, software, or any combination thereof. The pacer timing and control module may comprise a dedicated hardware circuit, such as an ASIC, separate from other processor 80 components, such as a microprocessor, or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber that is sensed, and the third letter may indicate the chamber in which the response to sensing is provided.

Intervals defined by the pacer timing and control module within processor 80 may include atrial and ventricular pacing escape intervals, refractory periods during which sensed P-waves and R-waves are ineffective to restart timing of the escape intervals, and the pulse widths of the pacing pulses. As another example, the pace timing and control module may define a blanking period, and provide signals sensing module 86 to blank one or more channels, e.g., amplifiers, for a period during and after delivery of electrical stimulation to heart 12. The durations of these intervals may be determined by processor 80 in response to stored data in memory 82. The pacer timing and control module of processor 80 may also determine the amplitude of the cardiac pacing pulses.

During pacing, escape interval counters within the pacer timing/control module of processor 80 may be reset upon sensing of R-waves and P-waves. Stimulation generator 84 may include pacer output circuits that are coupled, e.g., selectively by a switching module, to any combination of electrodes 34, 40, 42, 44, 46, 48, 50, 62, or 66 appropriate for delivery of a bipolar or unipolar pacing pulse to one of the chambers of heart 12. Processor 80 may reset the escape interval counters upon the generation of pacing pulses by stimulation generator 84, and thereby control the basic timing of cardiac pacing functions, including anti-tachyarrhythmia pacing.

The value of the count present in the escape interval counters when reset by sensed R-waves and P-waves may be used by processor 80 to measure the durations of R-R intervals, P-P intervals, PR intervals and R-P intervals, which are measurements that may be stored in memory 82. Processor 80 may use the count in the interval counters to detect an arrhythmia event, such as an atrial or ventricular fibrillation or tachycardia.

In some examples, processor 80 may operate as an interrupt driven device, and is responsive to interrupts from pacer timing and control module, where the interrupts may correspond to the occurrences of sensed P-waves and R-waves and the generation of cardiac pacing pulses. Any necessary mathematical calculations to be performed by processor 80 and any updating of the values or intervals controlled by the pacer timing and control module of processor 80 may take place following such interrupts. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. are incorporated herein by reference in their entireties. However, other arrhythmia detection methodologies may also be employed by processor 80 in other examples.

In the event that processor 80 detects an atrial or ventricular tachyarrhythmia based on signals from sensing module 86, and an anti-tachyarrhythmia pacing regimen is desired, timing intervals for controlling the generation of anti-tachyarrhythmia pacing therapies by signal generator 84 may be loaded by processor 80 into the pacer timing and control module to control the operation of the escape interval counters therein and to define refractory periods during which detection of R-waves and P-waves is ineffective to restart the escape interval counters.

If IMD 16 is configured to generate and deliver defibrillation pulses to heart 12, signal generator 84 may include a high voltage charge circuit and a high voltage output circuit. If IMD 16 is configured to generate and deliver pacing pulses to heart 12, signal generator 84 may include a low voltage charge circuit and a low voltage output circuit. In the event that generation of a cardioversion or defibrillation pulse is required, processor 80 may employ the escape interval counter to control timing of such cardioversion and defibrillation pulses, as well as associated refractory periods. In response to the detection of atrial or ventricular fibrillation or tachyarrhythmia requiring a cardioversion pulse, processor 80 may activate a cardioversion/defibrillation control module, which may, like pacer timing and control module, be a hardware component of processor 80 and/or a firmware or software module executed by one or more hardware components of processor 80. The cardioversion/defibrillation control module may initiate charging of the high voltage capacitors of the high voltage charge circuit of signal generator 84 under control of a high voltage charging control line.

Processor 80 may monitor the voltage on the high voltage capacitor may be monitored, e.g., via a voltage charging and potential (VCAP) line. In response to the voltage on the high voltage capacitor reaching a predetermined value set by processor 80, processor 80 may generate a logic signal that terminates charging. Thereafter, timing of the delivery of the defibrillation or cardioversion pulse by signal generator 84 is controlled by the cardioversion/defibrillation control module of processor 80. Following delivery of the fibrillation or tachycardia therapy, processor 80 may return signal generator 84 to a cardiac pacing function and await the next successive interrupt due to pacing or the occurrence of a sensed atrial or ventricular depolarization.

Signal generator 84 may deliver cardioversion or defibrillation pulses with the aid of an output circuit that determines whether a monophasic or biphasic pulse is delivered, whether housing electrode 34 serves as cathode or anode, and which electrodes are involved in delivery of the cardioversion or defibrillation pulses. Such functionality may be provided by one or more switches or a switching module of signal generator 84.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., electrocardiogram signals) produced by atrial and ventricular sense amp circuits within sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac events that sensing module 86 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

In other example examples, processor 80 may send impedance data to programmer 24 via telemetry module 88. For example, IMD 16 may send programmer 24 collected impedance measurements which are then analyzed by programmer 24. In such examples, programmer 24 performs the described processing techniques. Alternatively, IMD 16 may perform the processing techniques and transmit the processed impedance data to programmer 24 for reporting purposes, e.g., for providing an alert to patient 12 or another user.

As illustrated in FIG. 3, sensing module 86 may include an impedance measurement module 87. Processor 80 may control impedance measurement module 87 to periodically measure an electrical parameter to determine an impedance, such as a intrathoracic impedance. For a intrathoracic impedance measurement, processor 80 may control stimulation generator 84 to deliver an electrical signal between selected electrodes and impedance measurement module 87 to measure a current or voltage amplitude of the signal. Processor 80 may select any combination of electrodes 34, 40, 42, 44, 46, 48, 50, 62, 64, and 66, e.g., by using switch modules in signal generator 84 and sensing module 86. Impedance measurement module 87 includes sample and hold circuitry or other suitable circuitry for measuring resulting current and/or voltage amplitudes. Processor 80 determines an impedance value from the amplitude value(s) received from impedance measurement module 87.

In some examples, processor 80 may perform an impedance measurement by causing signal generator 84 to deliver a voltage pulse between two electrodes and examining resulting current amplitude value measured by impedance measurement module 87. In these examples, signal generator 84 delivers signals that do not necessarily deliver stimulation therapy to heart 12, due to, for example, the amplitudes of such signals and/or the timing of delivery of such signals. For example, these signals may comprise sub-threshold amplitude signals that may not stimulate heart 12. In some cases, these signals may be delivered during a refractory period, in which case they also may not stimulate heart 12.

In other examples, processor 80 may perform an impedance measurement by causing signal generator 84 to deliver a current pulse across two selected electrodes. Impedance measurement module 87 holds a measured voltage amplitude value. Processor 80 determines an impedance value based upon the amplitude of the current pulse and the amplitude of the resulting voltage that is measured by impedance measurement module 87. IMD 16 may use defined or predetermined pulse amplitudes, widths, frequencies, or electrode polarities for the pulses delivered for these various impedance measurements. In some examples, the amplitudes and/or widths of the pulses may be sub-threshold, e.g., below a threshold necessary to capture or otherwise activate tissue, such as cardiac tissue.

In certain cases, IMD 16 may measure intrathoracic impedance values that include both a resistive and a reactive (i.e., phase) component. In such cases, IMD 16 may measure impedance during delivery of a sinusoidal or other time varying signal by signal generator 84, for example. Thus, as used herein, the term "impedance" is used in a broad sense to indicate any collected, measured, and/or calculated value that may include one or both of resistive and reactive components.

In the example illustrated in FIG. 3, processor 80 and/or impedance analysis unit 92 are capable of performing the various techniques described in FIG. 1. To avoid confusion, impedance analysis unit 92 is described as performing the various impedance processing techniques proscribed to IMD 16, but it should be understood that these techniques may also be performed by processor 80. Although processor 80 and impedance analysis unit 92 are illustrated as separate modules in FIG. 3, processor 80 and impedance analysis unit 92 may be incorporated in a single processing unit.

In various example examples, impedance analysis unit 92 may perform one, all, or any combination of the plurality of impedance processing techniques discussed in greater detail below. In performing the processing techniques, IMD 16 may generate an alert upon determining that a decrease in impedance indicates that patient 14 is likely to experience a heart failure decompensation event. For example, IMD 16 may provide an audible or tactile alert in the form of a beeping noise or a vibrational pattern. Alternatively, IMD 16 may send an alert signal to programmer 24 that causes programmer 24 to provide an alert to patient 14. Programmer 24 may provide an audible, visual, or tactile alert to patient 14. Once patient 14 is alerted, he may then seek medical attention, e.g., by checking into a hospital or clinic.

The various components of IMD 16 are coupled to power source 90, which may include a rechargeable or non-rechargeable battery. A non-rechargeable battery may be capable of holding a charge for several years, while a rechargeable battery may be inductively charged from an external device, e.g., on a daily or weekly basis.

Figure 4:
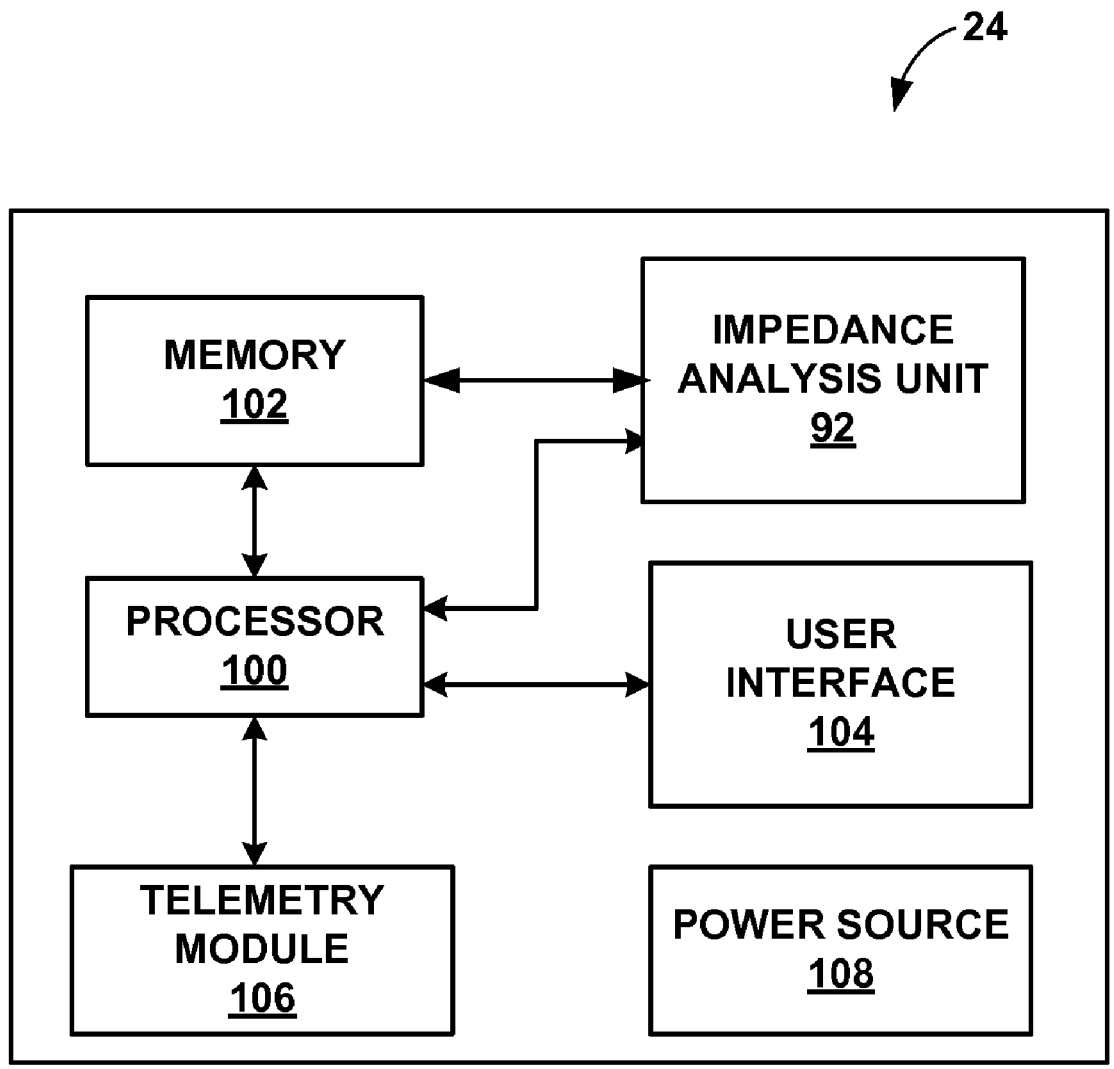
FIG. 4 is a functional block diagram illustrating an example configuration of the programmer shown in FIG. 1.

FIG. 4 is block diagram of an example programmer 24. As shown in FIG. 4, programmer 24 includes processor 100, memory 102, user interface 104, telemetry module 106, and power source 108. In some examples, programmer 24, as illustrated in FIG. 4, includes impedance analysis unit 92. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to configure any aspect of the impedance analysis techniques discussed herein. A user may also use programmer 24 to configure other sensing or any therapy provided by IMD 16. The clinician may interact with programmer 24 via user interface 104, which may include display to present graphical user interface to a user, and a keypad or another mechanism for receiving input from a user.

Processor 100 can take the form one or more microprocessors, DSPs, ASICs, FPGAs, programmable logic circuitry, or the like, and the functions attributed to processor 100 herein may be embodied as hardware, firmware, software or any combination thereof. Diagnostic unit 110, although illustrated as a separate module in FIG. 4, may be incorporated in a single processing unit with processor 100 or functional module executed or provided by processor 100. Memory 102 may store instructions that cause processor 100 and/or diagnostic unit 110 to provide the functionality ascribed to programmer 24 herein, and information used by processor 100 and/or diagnostic unit 110 to provide the functionality ascribed to programmer 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient. Memory 102 may also store information that controls operation of IMD 16, such as therapy delivery values.

A user, such as a clinician, technician, or patient 14, may interact with programmer 24 via user interface 104. User interface 106 may include display to present graphical user interface to a user, and a keypad or another mechanism for receiving input from a user. In some examples, user interface 106 may include a touch screen display.

Programmer 24 may communicate wirelessly with IMD 16, such as using RF communication or proximal inductive interaction. This wireless communication is possible through the use of telemetry module 106, which may be coupled to an internal antenna or an external antenna. An external antenna that is coupled to programmer 24 may correspond to the programming head that may be placed over heart 12, as described above with reference to FIG. 1. Telemetry module 106 may be similar to telemetry module 88 of IMD 16 (FIG. 3).

Programmer 24 may also be configured to communicate with another computing device via wireless communication techniques, or direct communication through a wired, e.g., network, connection. Examples of local wireless communication techniques that may be employed to facilitate communication between programmer 24 and another computing device include RF communication based on the 802.11 or Bluetooth specification sets, infrared communication, e.g., based on the IrDA standard.

Power source 108 delivers operating power to the components of programmer 24. Power source 108 may include a battery and a power generation circuit to produce the operating power. In some embodiments, the battery may be rechargeable to allow extended operation. Recharging may be accomplished by electrically coupling power source 108 to a cradle or plug that is connected to an alternating current (AC) outlet. In addition or alternatively, recharging may be accomplished through proximal inductive interaction between an external charger and an inductive charging coil within programmer 24. In other embodiments, traditional batteries (e.g., nickel cadmium or lithium ion batteries) may be used. In addition, programmer 24 may be directly coupled to an alternating current outlet to power programmer 24. Power source 108 may include circuitry to monitor power remaining within a battery. In this manner, user interface 104 may provide a current battery level indicator or low battery level indicator when the battery needs to be replaced or recharged. In some cases, power source 108 may be capable of estimating the remaining time of operation using the current battery.

In general, programmer 24 may receive impedance data from IMD 16 via telemetry module 106. As described previously, IMD 16 may periodically collect impedance data and then transmit the data to programmer 24. In some examples, IMD 16 may transmit the data in response to receiving a command from programmer 24. In the example illustrated in FIG. 4, programmer 24 may receive impedance data, such as measured intrathoracic impedance values or measured voltage/current values that may be used to calculate intrathoracic impedance, and analyze the received data by applying one, all, or any combination of the described impedance processing techniques. These processing techniques may be performed by processor 100 or impedance analysis unit 92. Moreover, similar to processor 80 (FIG. 3), impedance analysis unit 92 may, in some examples, be implemented in the physical processor represented by processor 100. In other example examples, programmer 24 may not include impedance analysis unit 92. In such example examples, the described impedance processing techniques are performed entirely by IMD 16 and programmer 24 receives the processed impedance data or alert indications from IMD 16 via telemetry module 106.

Although illustrated and described in the context of examples in which programmer 24 is able to program the functionality of IMD 16, in other examples a device capable of communicating with IMD 16 and providing functionality attributed to programmer 24 herein need not be capable of programming the functionality of the IMD. For example, an external home or patient monitor may communicate with IMD 16 for any of the purposes described herein, but need not independently be capable of programming the functionality of the IMD. Such as a device may be capable of communicating with other computing devices via a network, as discussed in greater detail below.

The components of and functionality provided by a diagnostic unit 92 for detecting worsening heart failure are described in greater detail below with respect to examples in which diagnostic unit 92 is located within IMD 16. However, it is understood that any one or more diagnostic units may be individually or collectively provided by any one or more devices, such as IMD 16 and programmer 24, to individually or collectively provide the functionality described herein.

Figure 5:
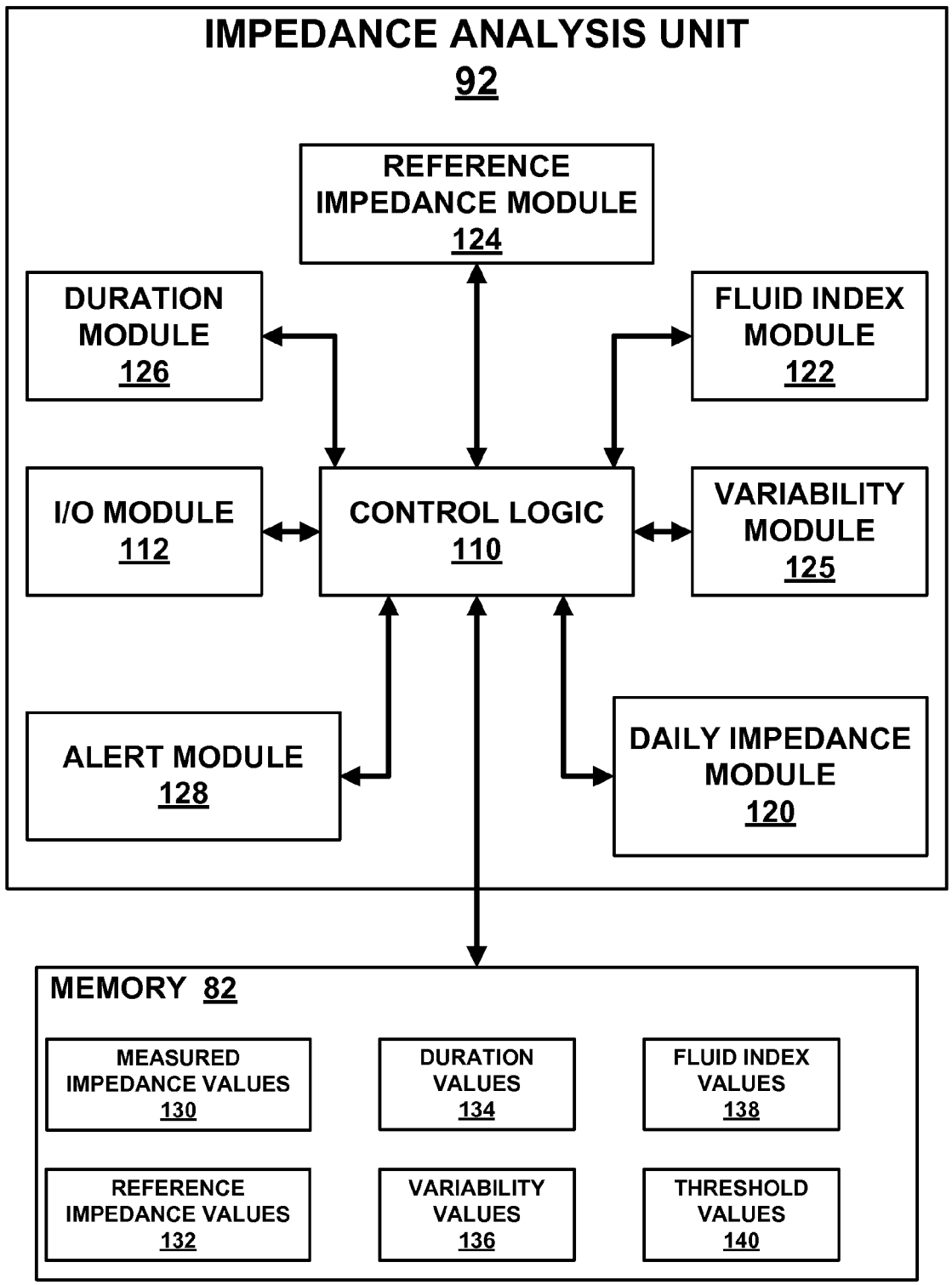
FIG. 5 is functional block diagram illustrating an example configuration of an impedance analysis module.

FIG. 5 is a block diagram of an example configuration of impedance analysis unit 92. As shown in FIG. 5, impedance analysis unit 92 includes multiple components including control logic 110, input/output (I/O) module 112, daily impedance module 120, fluid index module 122, reference impedance module 124, variability module 125, duration module 126, and alert module 128. Because either IMD 16 or programmer 24 may be configured to include impedance analysis unit 92, modules 110, 112, 120, 122, 124, 126, and 128 may be implemented in one or more processors, such as processor 80 of IMD 16 or processor 100 of programmer 24. Impedance analysis unit 92 is, in this example, shown in conjunction with memory 82 of IMD 16. The modules of impedance analysis unit 92 may be embodied as one or more hardware modules, software modules, firmware modules, or any combination thereof. Impedance analysis unit 92 may analyze impedance measurement data on a periodic basis to identify a decrease in intrathoracic impedance in patient 14 and alert patient 14 when the decrease indicates onset of a possible heart failure decompensation event.

In general, control logic 110 controls the operation of I/O module 112, daily impedance module 120, fluid index module 122, reference impedance module 124, variability module 125, duration module 126, and alert module 128. In particular, control logic 110 invokes each the modules so that they operate in a coordinated manner. Duration module 126 may include a counter on which control logic relies to invoke operation of the modules at appropriate times.

I/O module 112 allows impedance analysis unit 92 and, more particularly, control logic 110, to communicate with other modules, such as processor 80 and sensing module 86 of IMD 16 or processor 100 of programmer 24. Control logic 110 may monitor I/O module 112 for received data, such as impedance data that is measured periodically. I/O module 112 may send impedance data upon receiving a request from processor 80 or processor 100, such as when a user downloads data from IMD 16 or programmer 24, or may send data opportunistically, such as when an alert is provided to patient 14.

To implement the described impedance processing techniques, control logic 110 invokes I/O module 112 to receive impedances measured by impedance measurement module 87 and/or processor 80, and daily impedance module 120 to generate a measured impedance value from the received impedances. The measured values represent the intrathoracic impedance of patient 14.

Impedance measurement module 87 may measure impedance values on an hourly basis, daily basis, weekly basis, or the like. In one example, impedance measurement module 87 may measure impedance values during a particular portion of a day. As an example, impedance measurement module 87 may measure impedance values every twenty minutes for a predetermined number of hours, such as between noon and 5 pm. Daily impedance module 120 may determine a final measured impedance value by calculating an average of the measurements, in this case daily value that is the average of the impedances measured by impedance measurement module 87 during the day. The final averaged value may then be stored as a measured impedance value 130 in memory 82. Measured impedance values 130 may include the final averaged impedance value and a buffer for storing a number of measured values that are used for calculating the final averaged value. Measured impedance values 130 may also include a buffer of a plurality of past final averaged values. That is, measured impedance values 130 may include a buffer of past daily measured impedance values.

Variability module 125 may determine a variability value, VAR_VAL, based on the final averaged value and past daily measured impedance values. In particular, variability module 125 may compute the difference between the current measured impedance value and each of the values in the buffer of previous daily measured impedance values. Variability module 125 may then determine the median of these difference values. This value is referred to as "MED_VAR" and may be stored in memory 82 together with VAR_VAL as variability values 136. In some example examples, the variability value is not time dependent and, thus, MED_VAR=VAR_VAL. In other example examples, the variability value may be time dependent. In such examples, the time dependent value, VAR_FRAC, may be determined using a piecewise linear function, or any other mathematical function, e.g. an exponential decay. The variability value may be the product of median of the differences in daily impedance values and the time dependent value, i.e., VAR-VAL=MED_VAR*VAR_FRAC. An example piecewise linear function is:

$$VAR\_FRAC = \begin{cases} 0, & \text{if } x < 5 \text{ or } x > 90 \\ 1.25, & \text{if } 5 \leq x \leq 30 \\ 1.0, & \text{if } 30 < x \leq 60 \\ 0.5, & \text{if } 60 < x \leq 90 \end{cases}$$

where 'x' represents time measured in days from the start of the present fluid index event. During operation, duration module 126 may utilize a counter to keep track of the number of days passed since IMD 16 was implanted in patient 14 and store the value as duration value 134 in memory 114. Thus, impedance measurement module 120 may access the time value from memory 114 when calculating the variability value.

Reference impedance module 124 generates reference impedance values that are associated with the measured impedance values generated by daily impedance module 120. In particular, the reference impedance values generally track the trend of measured impedance values. As an example, reference impedance module 124 may calculate a reference impedance value by first retrieving the current impedance value and reference impedance value from memory 82 (stored as measured impedance values 130 and reference impedance values 132) and comparing the values to each other. Because the reference impedance value tracks the measured impedance value, the comparison may be used to determine whether to calculate the new or current reference value by either increasing or decreasing the old or previous reference impedance value. Current and previous reference values are stored in memory 114 as reference impedance values 132.

Reference impedance module 124 may also store a plurality of increment and decrement values, referred to as slope values, in memory 82. The slope values are used to calculate a current reference impedance value from a previous reference impedance value. The plurality of slope values is comprised of a plurality of groups of slope values. Each group of slope values corresponds to a period of time and includes a predetermined increment value and a predetermined decrement value.

Reference impedance module 124 selects a particular group based on the time and selects either the first or second slope value from the selected group based on the comparison of the current measured impedance value 130 to the corresponding reference impedance value 132. Reference impedance module 124 selects the increment value from the selected group when the current measured impedance value is greater than the reference impedance value. Similarly, when the current measured impedance value is less than the reference impedance value, reference impedance module 124 selects the decrement value from the selected group.

Reference impedance values 132 may, for example, store three groups of slope values. A first group may be utilized during the first 60 days following implantation of IMD 16 in patient 14. The second group may be utilized during the $60^{th}$ through the $100^{th}$ days. The third group may be utilized after the $100^{th}$ day. These periods are merely examples, and other periods and numbers of slope value groups are contemplated.

In general, the absolute values of the increment values for the groups decrease relative to time and the absolute value of the decrement values for the groups increase relative to time. In other words, using the previous example, the increment value of the first group is larger than the increment values of the second and third groups and increment value of the second group is larger than that of the third group. In a similar fashion, the decrement value of the first group results in the smallest decrease in reference impedance while the decrement value of the third group results in the largest decrease in reference impedance.

Selecting slope values in this way may allow for more accurate tracking of intrathoracic impedance of patient 14 as the device pocket dries out following implantation of IMD 16. This is because the fluid build-up in the device pocket immediately following the implant procedure results in a lower impedance than normal. As the fluid dissipates the impedance increases. The rate at which the fluid dissipates decrease as time elapses so it may be desirable for the reference impedance to be able to increase at a greater rate immediately following implant than after 60 or 100 days have passed. Similarly, it may be desirable to change the rate at which the reference impedance decreases over time so that larger decreases in reference impedance are possible as time progresses.

Duration module 126 may implement as a counter (COUNT) that counts the number of days since the fluid index began computing. In other words, duration module 126 counts the number of days since the measured impedance (or a mean or other value determined based thereon) was less than the reference impedance. Keeping track of the number of days since the fluid index began computing may be important for categorizing the type of event. For example, if a decrease in impedance occurred over only a few days the event may be categorized as being consistent with patient 14 failing to take medication or may be categorized as an acute decompensation that may lead to medical intervention. On the other hand, if a decrease in impedance occurred over an extended period of time before system 10 provides an alert to patient 14, the event may be categorized as a series of small DC shifts in impedance. Such events are generally considered nonthreatening and may not require patient 14 to seek medical attention.

In some examples, duration module 126 may also compute a time dependent value used for calculating the fluid index. The time dependent value (DURATION) may be added to the fluid index depending on the time that the fluid index has maintained a positive value without resetting. DURATION may increase as a linear, piecewise linear, exponential, or other function of COUNT.

Fluid index module 122 computes the fluid index using measured and reference impedance values stored in memory 114, i.e., measured impedance values 130 and reference impedance values 132. Fluid index module 122 may store the computed value as fluid index value 138 in memory 82. In general, fluid index module 122 computes the fluid index as some function of the difference between the measured impedance value and the reference impedance value when the measured impedance value is less than the reference impedance value. As an example, fluid index module 122 may compute the fluid index simply as the difference between the measured impedance value and the reference impedance value when the measured impedance value is less than the reference impedance value.

In some examples, fluid index module 122 may not begin computing the fluid index value immediately after implant of IMD 16 in patient 14. Rather, control logic 110 may invoke fluid index module 122 after a period of time has elapsed. The period of time may be several days, a week, several weeks, or the like. In one example, fluid index module 122 may begin computing the fluid index value on day 34 following implant of IMD 16. It should be understood that other methods of computing the fluid index are possible and within the scope of this disclosure but are not described in the interest of brevity.

Because reference impedance module 124 also compares the measured impedance value to the reference impedance value, fluid index module 122 may store and update a flag variable in fluid index values 138 that indicates whether the measured reference value is greater than or less than the reference impedance value. In such cases, reference impedance module 124 may check the flag variable rather than compare the measured impedance value to the reference impedance value.

In any case, fluid index module 122 may compute the fluid index over a finite period of time that functions as a sliding window over which the fluid is computed. For example, fluid index module 122 may compute the fluid index daily over a period of several days, a week, or more. In such example examples, fluid index module 122 may store a buffer of daily fluid index values as fluid index values 138 in memory 82. The buffer stores the previous number of daily fluid index values. The total fluid index value (FI_TOT) is the sum of the all the daily fluid index values in the buffer. Fluid index module 122 may reset the fluid index, i.e., reset the buffer, when the daily measured impedance value is greater than or equal to the reference impedance value.

In some examples, fluid index module 122 may, as previously described, include the variability value (VAR_VAL), the duration value (DURATION), or both in determining the fluid index. In such examples, the variability value and duration value are factored into the daily fluid index value.

Alert module 128 may compare the total fluid index value from fluid index module 122 to one or more threshold values 140 to determine whether to provide an alert to patient 14 to indicate the possible onset of a heart failure decompensation event. For example, alert module 128 may retrieve a first threshold value, a second threshold value, and the fluid index value from memory 82 and compare the fluid index value to the threshold values. Initially, alert module 128 compares the fluid index value to the first threshold value. When the fluid index value is greater than the first threshold value, alert module 128 may output an alert signal that is received by control logic 110. Control logic 110, in response to receiving the alert signal, transmits a command via I/O module 112 to processor 80 or processor 100 that causes IMD 16 or programmer 24, respectively, to provide an alert to patient 14 or another user.

The second threshold value is less than the first threshold value and is used as a secondary comparison to provide a margin of error or buffer around the first threshold value. That is, because the fluid index value is computed using a sliding window the fluid index may "hover" near the first threshold value. As a result, the fluid index value may decrease a small amount that is just enough for the fluid index value to remain less than the first threshold value. Without the second threshold value the fluid index value would be compared only the first threshold value and the result would be that no alert would be provided to patient 14. However, this issue is reduced by comparing the fluid index value to the second threshold value because alert module 128 may output the alert signal as long as the fluid index value remains greater than the second threshold value. The second threshold value may be set to zero when the fluid index value resets.

Because alert module 128 may only compare the fluid index value to the second threshold value after the fluid index value has been determine to be greater than the first threshold value, alert module 128 may store a flag variable as fluid index values 140 in memory 114 and reference the flag variable to determine when the fluid index should be compared to the second threshold value.

Impedance analysis unit 92, as shown in FIG. 5, is configured to implement all of the impedance processing techniques described in this disclosure. It should be understood, however, that FIG. 5 is merely an example configuration and that impedance analysis unit may also be configured to implement one, or any combination of, the described processing techniques.

Figure 6:
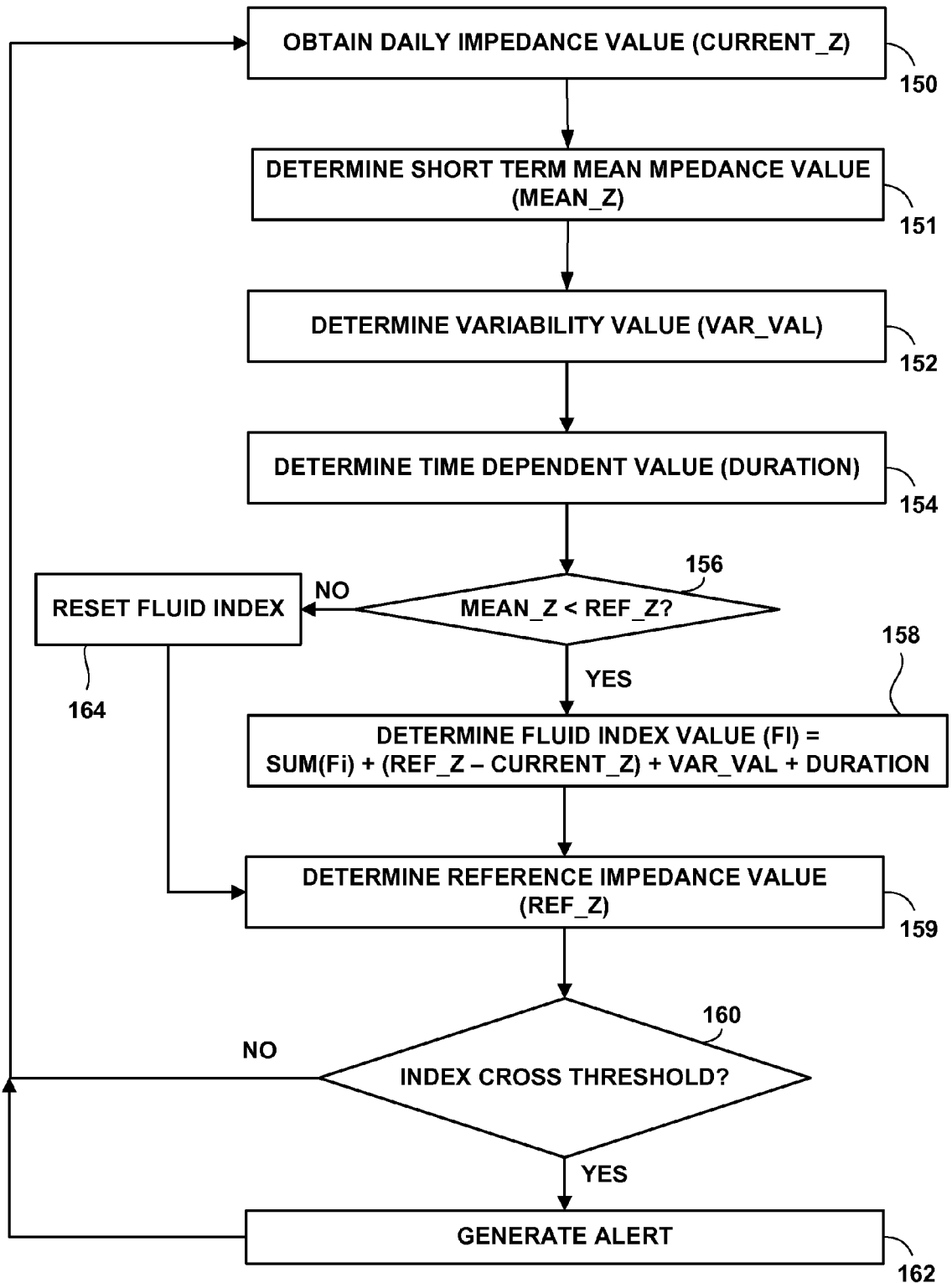
FIGS. 6-11 are flow diagrams illustrating example methods that may be performed by one or both the IMD and programmer shown in FIG. 1 to provide alert to the patient upon detection of a possible heart failure decompensation event.

FIG. 6 is a flow diagram illustrating an example method for detecting the onset of a possible heart failure decompensation event and providing an alert to patient 14 upon detection of such an event. In various examples, the illustrated method may be performed by IMD 16, external programmer 24, or a combination of both. For example, IMD 16 may collect impedance data, measure the intrathoracic impedance of patient 14 based on the impedance data, and process the impedance data with processor 80 and/or impedance analysis unit 92 in accordance with the method shown in FIG. 6. In another example, IMD 16 may collect impedance data and send the impedance data to external programmer 24 for processing in the manner shown in FIG. 6. For purposes of illustration only, it will be assumed in the subsequent description that IMD 16 performs the method shown in FIG. 6. It will also be assumed that the illustrated method may be performed repeatedly over multiple periods of time, e.g., multiple times per day, on a daily basis, or the like.

In general, the method show in FIG. 6 is one example method that may be performed by IMD 16. The example method provides for applying each of the processing techniques described in this disclosure, i.e., processing measured impedance values to determine a variability value used for determining the fluid index, processing measured impedance values to determine a time dependent value used for determining the fluid index, determining the fluid index over a finite period of time, selecting time dependent reference impedance values used for determining the fluid index, and comparing the fluid index to a plurality of threshold values to determine whether to provide an alert to patient 14. IMD 16, however, may implement any number or combination of the described techniques. The methods for performing the described techniques are shown in greater detail in FIGS. 7-11.

Initially, IMD 16 obtains a current impedance value (CURRENT_Z) (150). IMD 16 may measure impedance value by collecting impedance data for one or more electrical paths provided by housing electrode 34 and the electrodes on leads 18, 20, and 22 and determining impedance values from the impedance data. The current impedance value may be obtained from a plurality of measured impedance values. For example, IMD 16 may measure the intrathoracic impedance of patient 14 several times per day. As previously described, the measured impedance values may be collected at a regular intervals throughout the day or during a particular portion of the day. In one example, IMD 16 may calculate the current impedance value as the average of impedance values measured every 20 minutes from the hours of 12 p.m. to 5 p.m.

IMD 16 may then determine a short term mean impedance value (MEAN_Z) (151). The short term mean may be the mean or weighted mean of the CURRENT_Zs from a plurality of days, e.g., the last three or four days. To determine the current and mean impedances, impedance analysis unit 122 may employ the techniques described in U.S. application Ser. No. 10/727,008 by Stadler et al., entitled "METHOD AND APPARATUS FOR DETECTING CHANGE IN INTRATHORACIC IMPEDANCE," filed on Dec. 3, 2003, and incorporated herein by reference in its entirety.

IMD 16 may then determine a variability value (VAR_VAL) based on the measured impedance value (CURRENT_Z) (152). In one example, the variability value may be time dependent. In such example examples, the variability value may be scaled by a time dependent factor, such as VAR_FRAC that is calculated according to the previously provided piecewise linear function, that is selected based on the length of time that has elapsed since implant of IMD 16 in patient 14. Generally, the time dependent value is used to scale the variability value over time such that the fluid index accumulates less in patients with higher day to day variability in the periodic impedance measurements. The variability value is used to determine the fluid index. An example method for determining the variability value is shown in greater detail in FIG. 7.

IMD 16 may also determine a time dependent value, referred to as a duration value, (DURATION) used for calculating the fluid index (154). The duration value generally increases over time. This results in the fluid index increasing at a greater rate as the impedance of patient 14 continually decreases. As previously described, the duration value may be determined based on the number of days that the fluid index has been accumulating without resetting. An example method of determining the duration value is shown in greater detail in FIG. 8.

IMD 16 compares the short term mean impedance value to a reference impedance value (156). When the short term mean impedance value is greater than the reference impedance value, IMD 16 resets the fluid index (164). When the short term mean impedance value is less than the reference impedance value, IMD 16 determines the fluid index (158).

Figure 9:
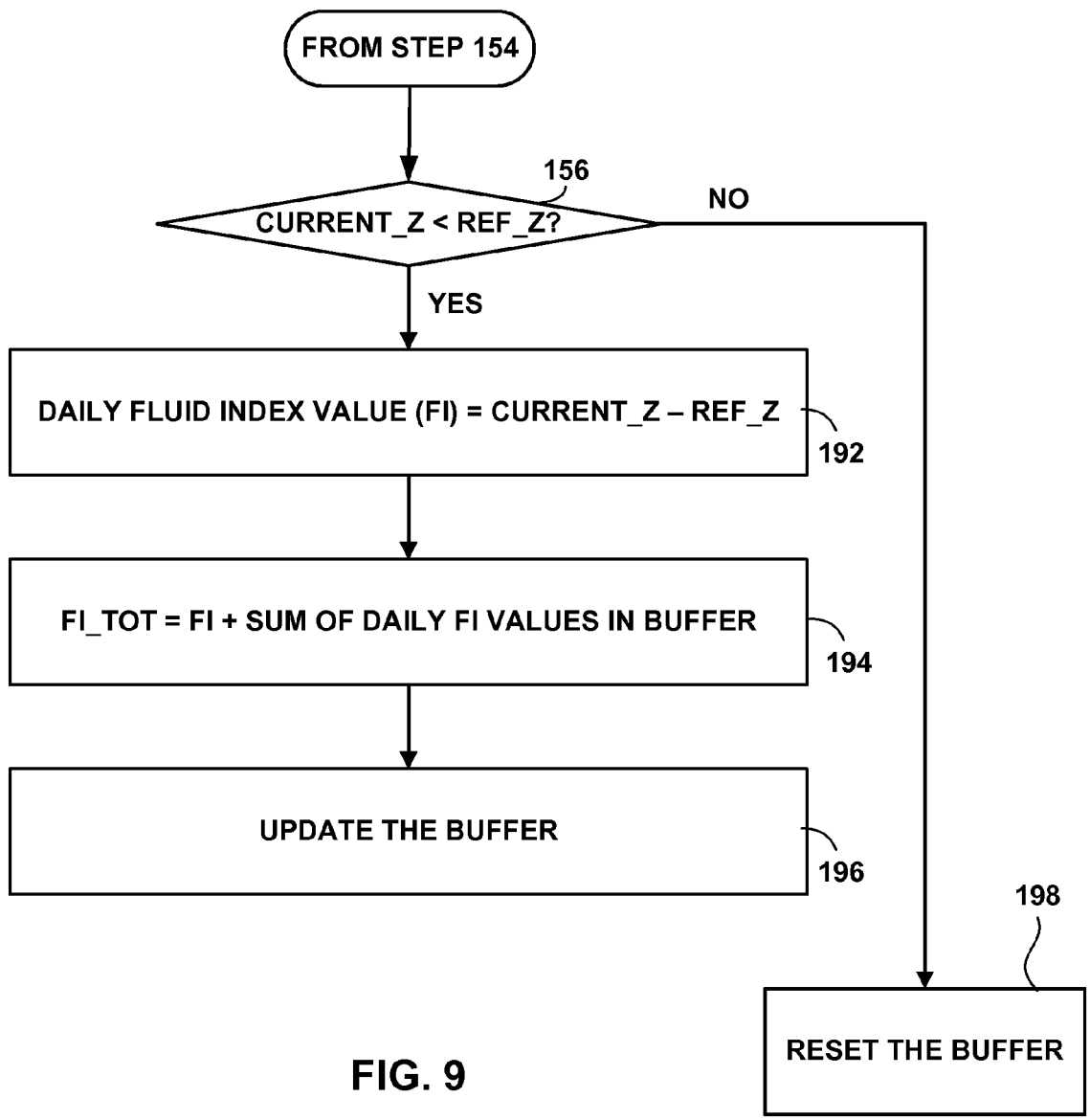

IMD 16 may determine the fluid index (FI) over a finite period of time based on the current impedance value, the reference impedance value, the variability value, and the duration value. The finite period of time may be a period of a few days, a week, or more and functions as a sliding window over which the fluid index is determined based on intrathoracic impedance measurements and, thus, patient condition in the recent past. Using a week as an example finite period of time and determining the fluid index daily, the total fluid index value may then be determined as the sum of the six previous daily fluid index values and the current impedance value. In examples in which the variability value and the duration value are determined, these values are also included in determining the fluid index. Duration may be summed into the fluid index, as illustrated in FIG. 6, or the difference between the reference and current impedances may be multiplied by a factor that is dependent on duration. FIG. 9 provides a more detailed method for determining the fluid index.

Next, IMD 16 may determine a reference impedance value (159). The reference impedance value is used in the following iteration of the illustrated method. Generally, reference impedance values are used for tracking the trend of measured impedance values. As previously described, IMD 16 may employ an adaptive processing technique that determines reference impedance values in a way that allows for different rates of change over time. An example method for determining reference impedance values is shown in greater detail in FIG. 10.

Finally, IMD 16 may compare the fluid index to a plurality of threshold values to determine whether to provide an alert (160). In general, IMD 16 provides an alert when the fluid index crosses a threshold value. For example, as previously described, IMD 16 generates an alert (162) when the fluid index is greater than the primary threshold value and when fluid index is greater than the secondary threshold value if the fluid index was greater than the primary threshold value during a previous iteration.

Figure 7:
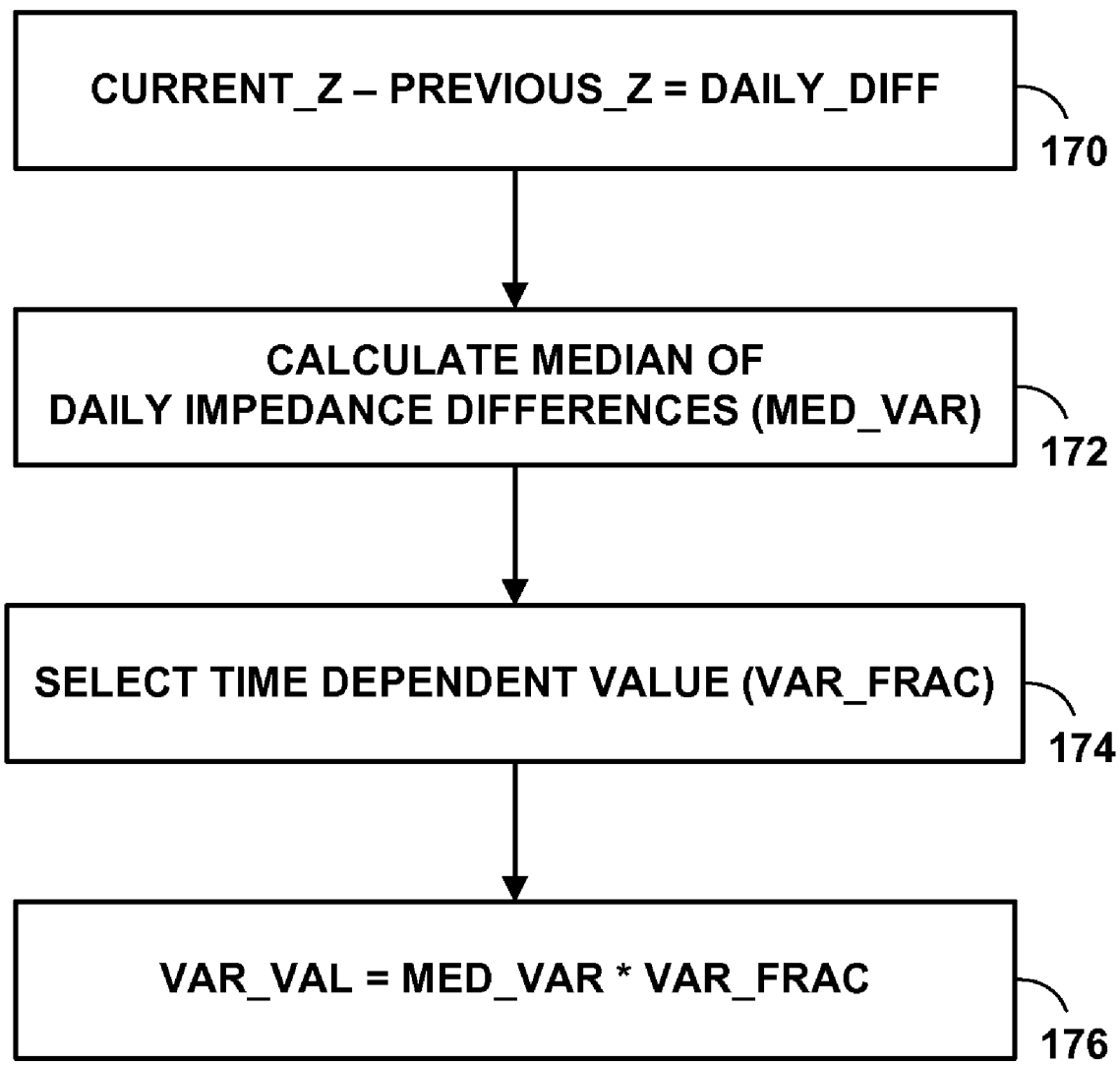

FIG. 7 is a flow diagram illustrating an example method for determining a variability value used for calculating the fluid index. This method may be used for determining the variability value as shown in step 152 of the method illustrated in FIG. 6.

According to the example method, IMD 16 computes the day to day impedance difference (170). The impedance difference is computed as the difference of the current impedance value for the current day to the "current" impedance value for the previous day. As previously described, the impedance differences may be stored in a buffer which stores a predetermined number of impedance differences. IMD 16 may then use the values stored in the buffer to calculate the median of the impedance differences (MED_VAR) (172). Thus, the median variability may be determined based on variability in the recent past, e.g., in the last X days.

In some examples, IMD 16 calculates a time dependent value (VAR_FRAC) that is used to scale the median of impedance values (174). This scaling value generally increases the resulting variability value over time so that the fluid index accumulates less in patients with a higher day to day variability in impedance measurements and may be calculated according to the piecewise linear function provided in this disclosure. IMD 16 may scale the median of the impedance differences to calculate the variability value (VAR_VAL)

(176). IMD 16 may then use the variability value in determining the fluid index (156 of FIG. 6).

Figure 8:
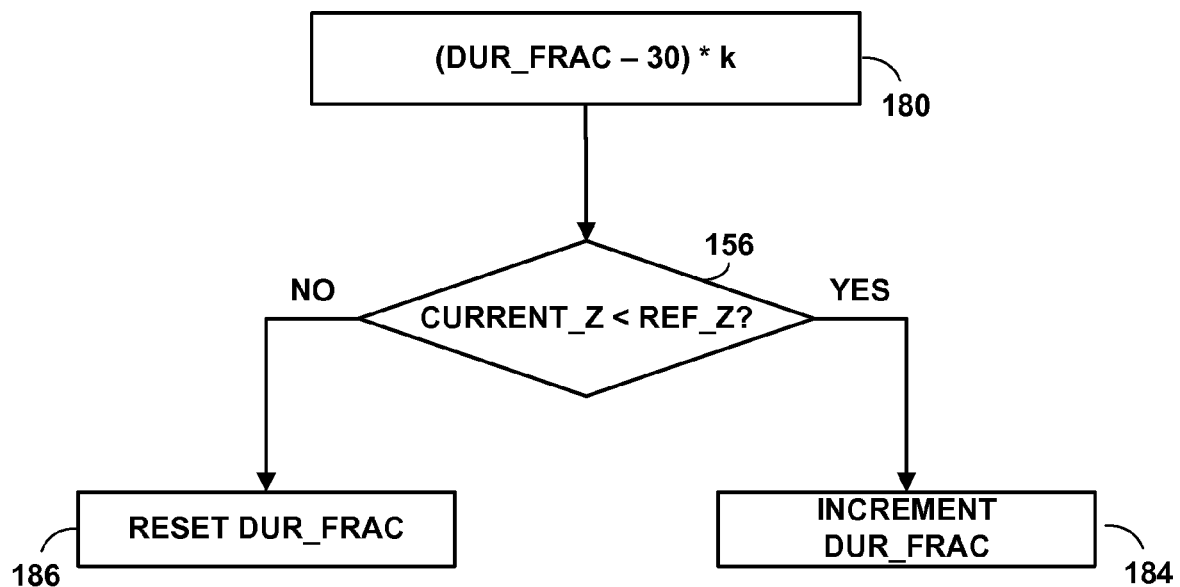

FIG. 8 is a flow diagram illustrating an example method for determining a duration value (154 of FIG. 6) used for calculating the fluid index. According to the example method, IMD 16 determines the duration value (180). IMD 16 may determine the duration value according to the illustrated equation, where DUR_FRAC represents the length of time that the fluid index has had a value greater than zero without resetting and "k" is a constant scaling factor.

Next, IMD 16 may compare the current impedance value to the corresponding reference impedance value (156). When the current impedance is less than the reference impedance, IMD 16 updates or increments the counter DUR_FRAC (184). If, however, the current impedance is greater than the reference impedance, IMD 16 resets the counter (186). This is because, in accordance with FIG. 6, the fluid index is also reset when the current impedance is greater than the reference impedance.

FIG. 9 is a flow diagram illustrating an example method for determining the fluid index (FI) (158 of FIG. 6) based on a finite number of previous measured and reference impedances, e.g., over a finite period of time in the recent past. According to the illustrated example, IMD 16 compares the current impedance to the reference impedance (156). When the current impedance is less than the reference impedance, IMD 16 calculates the daily fluid index value (192). The daily index value may be adjusted based on a variability value, as discussed above. IMD 16 then calculates the fluid index value, i.e., the total fluid index value (FI_TOT) as the sum of the daily fluid index values stored in a buffer and the current daily fluid index value (194). The fluid index value may be adjusted based on a duration value, as discussed above. IMD 16 may then update the buffer to include the current daily fluid index value (196). Because the size of the buffer is constant, the buffer operates as a sliding window in time over which the fluid index is determined, e.g., as the current daily fluid index is added, the least recent value in the buffer is removed. However, when the current impedance is greater than the reference impedance, IMD 16 resets the fluid index buffer (198).

Figure 10:
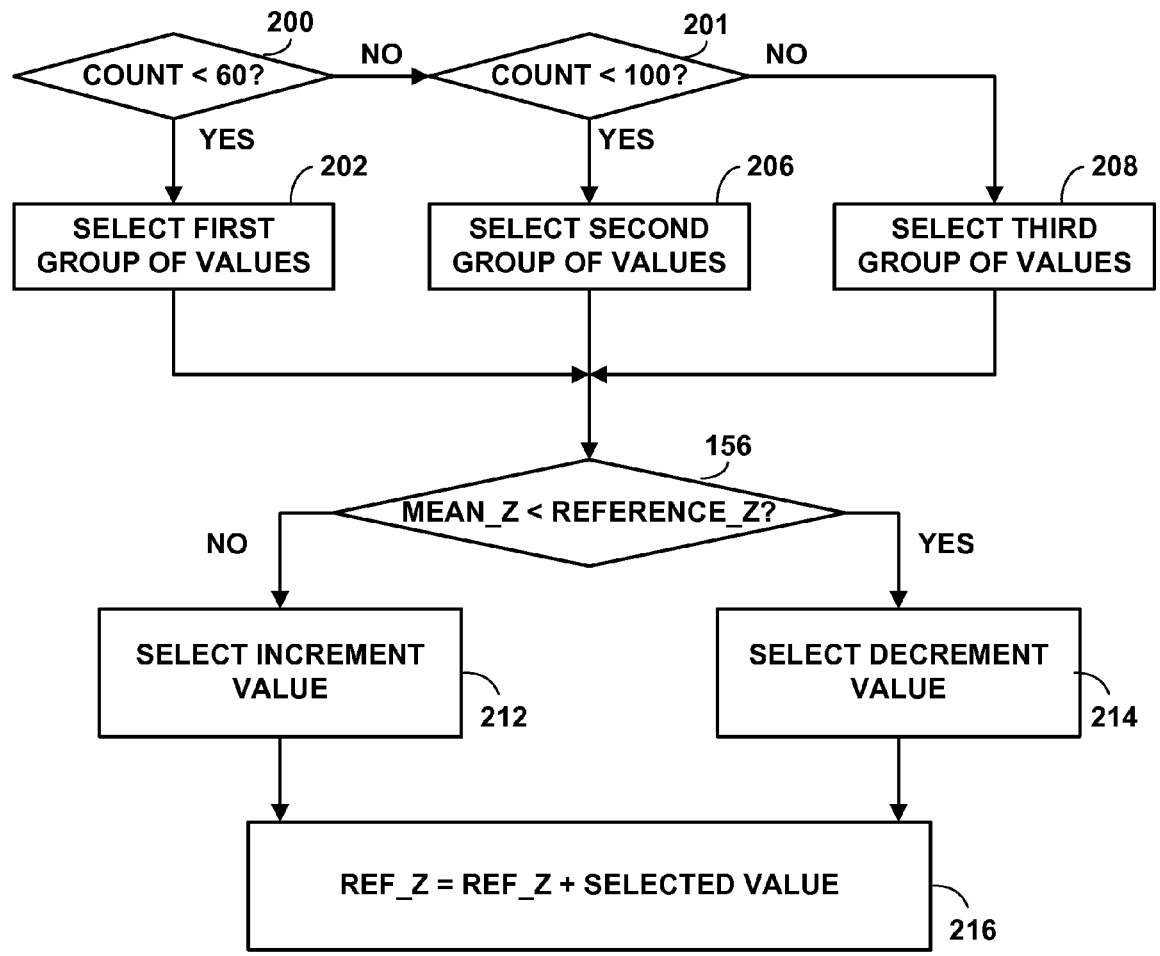

FIG. 10 is a flow diagram illustrating an example method for determining reference impedance values (159) used for tracking the trend of measured impedance values. In general, the method illustrated in FIG. 10 allows for adapting the rate of change of the reference impedance over time. In particular, this method allows for the reference impedance to increase and decrease at different rates over the same period of time and to increase and decrease at different rates over time. As previously described, this is achieved by storing groups of preselected or predetermined increment and decrement values. Each group of values corresponds to a specific period time. The increment value of each group is used as a positive slope value, i.e., used to increase the value of the reference impedance. The decrement value of each group is used as a negative slope value, i.e., used to decrease the value of the reference impedance.

The example method illustrated in FIG. 10, begins 34 days after IMD 16 is implanted in patient 14 and uses three groups of preselected increment and decrement values. In other examples, the method may begin after a lesser or greater number of days following the implant procedure, or may begin immediately following the implant procedure. In other examples, the method may also utilize two groups of slope values or more than three groups of slope values. With respect to FIG. 10, IMD 16 first compares the number of days since the implant procedure or a reference reset after system modification, represented by COUNT, to a threshold value (200), which is 60 in this case. Thus, if COUNT is greater than 34 and less than 60, then IMD 16 selects the first group of increment and decrement values 202.

If, however, COUNT is greater than 60, IMD may then compare the number of days to another value, which is 100 in the illustrated example (201). When COUNT is greater than 60 and less than 100, IMD 16 selects the second group of increment and decrement values (206). If, however, COUNT is greater than 100, then IMD 16 selects the third group of increment and decrement values (208).

After IMD 16 selects a group of increment and decrement values, IMD 16 compares the short term mean impedance (discussed above) to the reference impedance (156). Based on this comparison, IMD determines whether to increase or decrease the reference impedance to track the measured impedance. Accordingly, IMD 16 selects the increment value (212) of the selected group when the current impedance is greater than the reference impedance. When the current impedance is less than the reference impedance, IMD 16 selects the decrement value (214). IMD 16 determines the "current" reference impedance by adding the selected value to the "previous" reference impedance (216). IMD 16 may then use the reference impedance, together with a new current measured impedance, to determine the fluid index.

Figure 11:
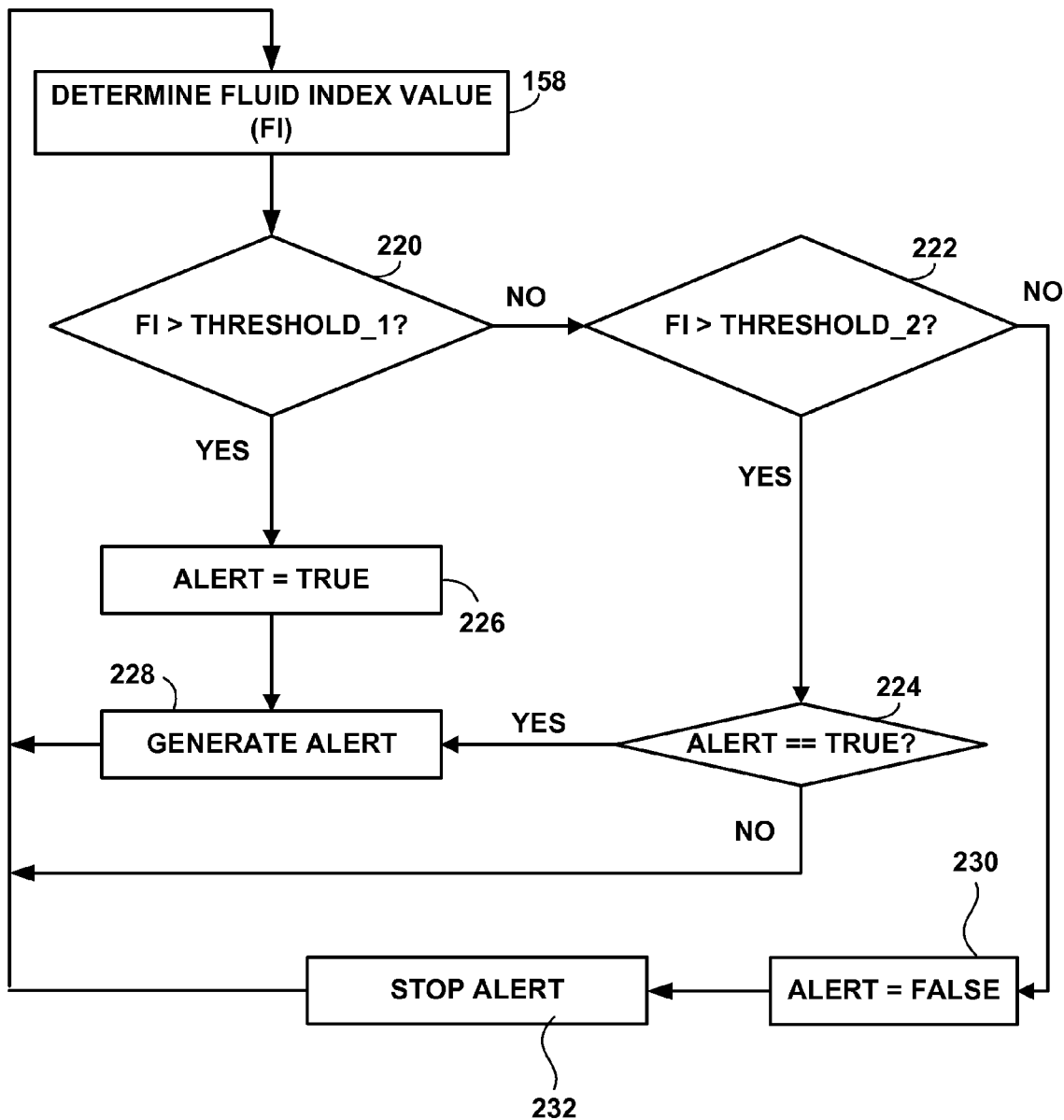

FIG. 11 is a flow diagram illustrating an example method for determining when to provide an alert (160 of FIG. 6) to patient 14. In general, the method illustrated in FIG. 11 is useful in combination with the method used for determining the fluid index over a finite period of time (FIG. 9). This is because the plurality of threshold values provides a margin of error or range of values over which to provide an alert to patient 14. In particular, a first threshold value is used as a bright line to determine whether the fluid index indicates the onset of a heart failure decompensation event and the second threshold value is used to allow for small fluctuations in the fluid index while continuing to provide an alert to patient 14. In other words, the plurality of threshold values allow for providing a continuous alert while the fluid index fluctuates or varies around a point of interest. Without using a plurality of threshold values, the alert may be generated "sporadically" as the fluid index fluctuates around the point of interest over time. A continuous alert may be more favorable than a sporadic alert because a continuous alert may cause patient 14 to seek medical attention more quickly and/or reduce the possibility that an otherwise sporadic alert would be interpreted as an error rather than an indication of the onset of a heart failure decompensation event.

In the example method illustrated in FIG. 11, IMD 16 may initially set a flag variable, ALERT, to a false value. IMD 16 determines the fluid index (158) as discussed above with reference to FIG. 6. IMD 16 may compare the fluid index (FI) to the first threshold value, THRESHOLD_1$f$ (220). When the fluid index is greater than the first threshold value, IMD 16 sets ALERT to a true value (226) and generates an alert (228). However, when the fluid index is less than the first threshold value, IMD 16 compares the fluid index to the second threshold value, THRESHOLD_2 (222). If the fluid index is greater than the second threshold value, then IMD 16 examines the ALERT flag variable (224) to determine whether the fluid index was greater than the first threshold value in a previous iteration. When ALERT has a true value the fluid index was greater than the first threshold value in a previous iteration, and IMD 16 continues to generate the alert (228). However, when ALERT has a false value, i.e., the fluid index value was less than the first threshold value in the previous iteration and IMD 16 takes no action until determination of a next fluid index value. If, however, the fluid index is less than the second threshold value, then IMD 16 sets ALERT to a false value (230) and may stop the alert (232). In this way, IMD 16 generates an alert when the fluid index value is greater than the first threshold value and when the fluid index value is greater than the second threshold value after the fluid index was greater than the first threshold value during a previous iteration. IMD 16 may, at this time, also reset the fluid index (164).

Figure 12:
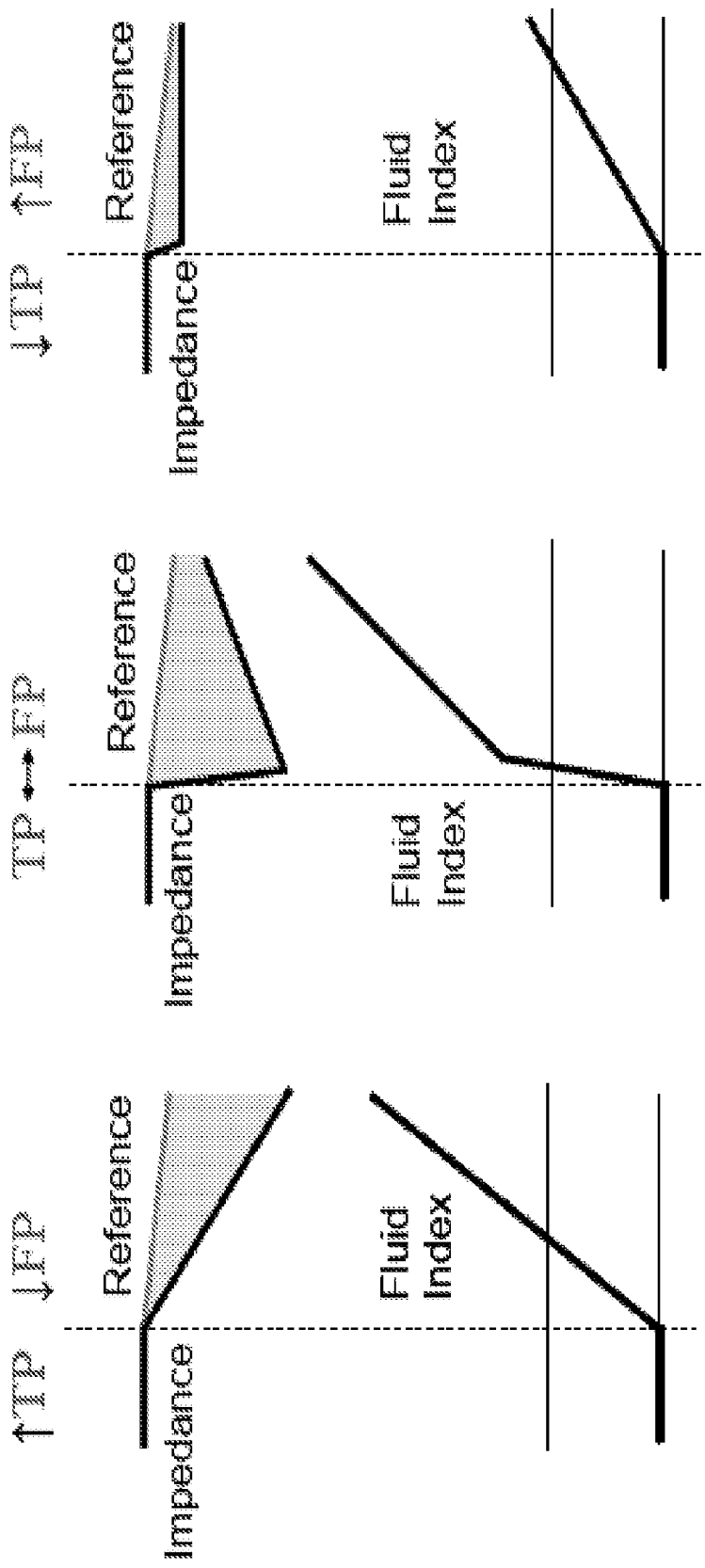
FIGS. 12A-12C are timing diagrams illustrating example of changing impedance over time.

FIGS. 12A-12C are timing diagrams illustrating examples of changing impedance over time. The three timing diagrams of FIGS. 12A-12C correspond to the three dominant morphologies of impedance decreases discussed above.

For example, FIG. 12A illustrates a gradual and consistent decrease in impedance over an extended period of time. The duration of this type of impedance decrease is longer than a month. This impedance decrease is strongly associated with worsening cardiac heart failure.

FIG. 12B illustrates a sudden drop in impedance followed by a trend of increasing impedance back towards the baseline impedance. This type of event may result from changes in patient compliance behaviors, such as medication or dietary indiscretion, or result from acute decompensation that may lead to medical intervention. Thus, some impedance decreases of this type may be critical while others may be less critical.

FIG. 12C illustrates an impedance decrease resulting from small DC shifts in impedance. Because these small shifts may occur several times, they may eventually lead to threshold crossings and resulting alerts if the fluid index is accumulated over a long period of time. For example, a sustained shift in impedance of even two or three ohms may result in a crossing if sustained for a sufficient period of time. The standard deviation of day to day variation in impedance has been observed to be on the order of three ohms. Thus, this class of decrease in impedance is not considered clinically critical but can lead to false alerts if the processing technique is not properly designed.

Figure 13:
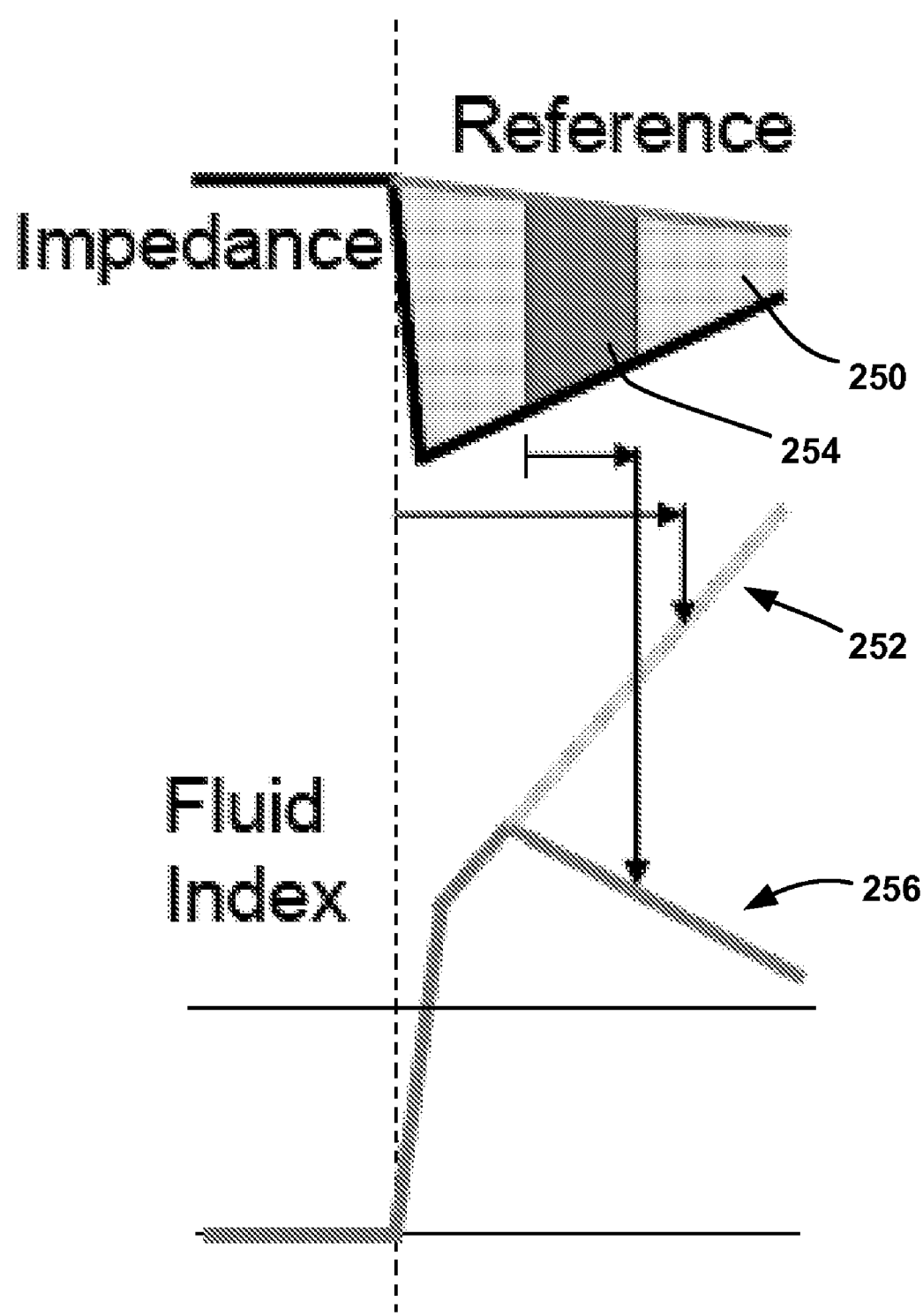
FIG. 13 is a timing diagram illustrating use of a finite buffer to limit accumulation of a fluid index over time.

FIG. 13 is a timing diagram illustrating use of a finite buffer to limit accumulation of a fluid index over time. FIG. 13 illustrates a sudden drop in impedance followed by a trend of increasing impedance back towards the baseline impedance, similar to FIG. 12B discussed above.

In an example in which a finite buffer would not be used, all differences between the measured impedances and reference impedances while the measured impedances are less than the reference impedances, as indicated by the lighter shaded area 250 between the measured and reference impedances, are summed. As a result, the corresponding fluid index 252 continues to increase, despite increasing impedance, which may indicate an improvement in patient condition due to, for example, improved compliance with medication or diet. Accordingly, an IMD or other device may provide an alert, due to the fluid index 252 crossing a threshold, while the patient's condition is actually improving.

In an example in which a finite buffer is used, a finite number, e.g., sliding window, of differences between the measured impedances and reference impedances while the measured impedances are less than the reference impedances, as indicated by the darker shaded area 254 between the measured and reference impedances, are summed. As a result, the corresponding fluid index 256 begins to increase while the measured impedances increase and the condition of the patient improves. Accordingly, an IMD or other device may avoid providing an alert while the patient's condition is actually improving.

Figure 14:
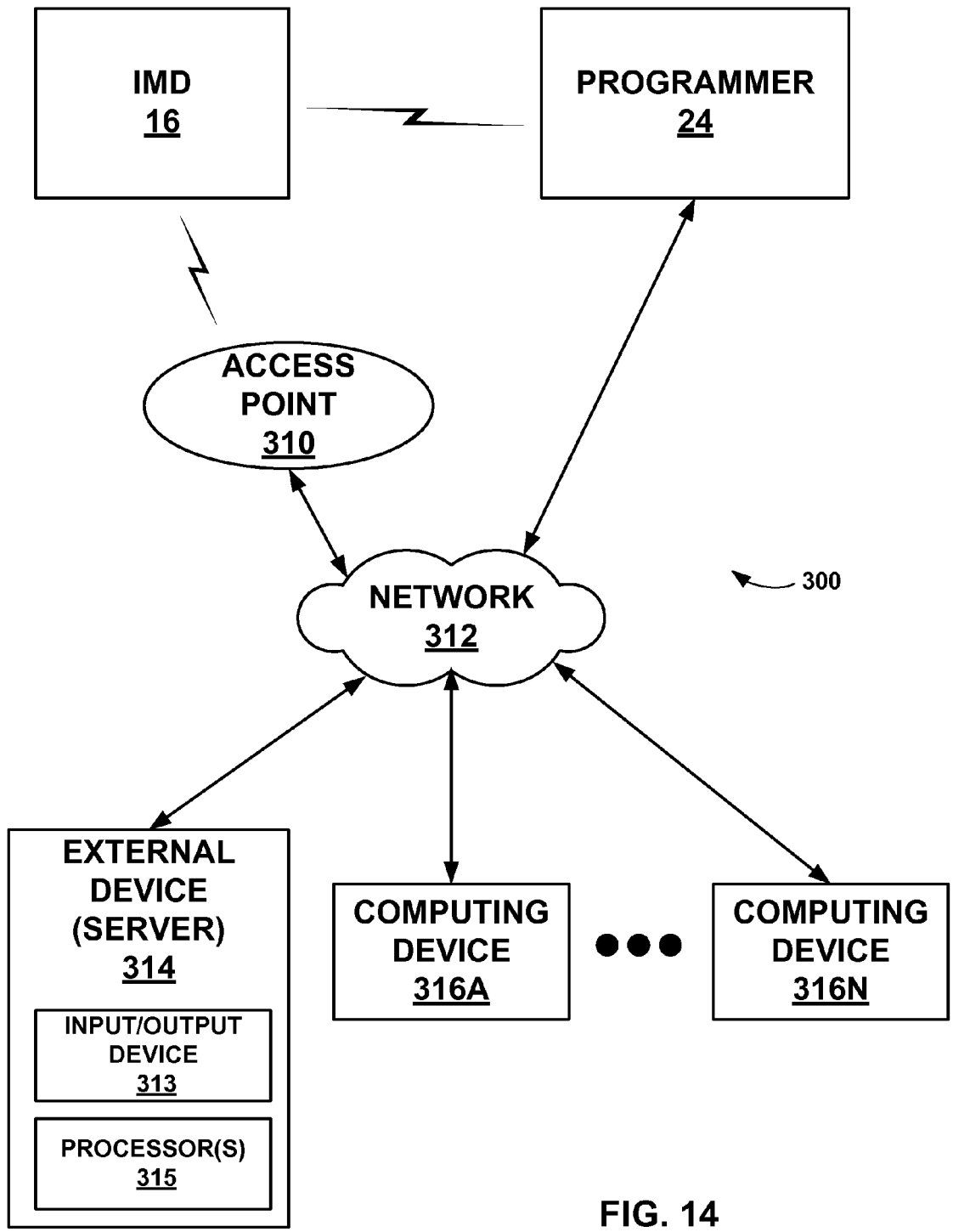
FIG. 14 is a block diagram illustrating an example system that includes an external device, such as a server, and one or more computing devices that are coupled to the IMD and programmer shown in FIG. 1 via a network.

FIG. 14 is a block diagram illustrating an example system 300 that includes an external device, such as a server 314, and one or more computing devices 316A-316N ("computing devices 316") that are coupled to IMD 16 and programmer 24 shown in FIG. 1 via a network 312. In this example, IMD 16 may use its telemetry module 88 to communicate with programmer 24 via a first wireless connection, and to communication with an access point 310 via a second wireless connection. In the example of FIG. 14, access point 310, programmer 24, server 314, and computing devices 316A-316N are interconnected, and able to communicate with each other, through network 312. In some cases, one or more of access point 310, programmer 24, server 314, and computing devices 316A-316N may be coupled to network 312 through one or more wireless connections. IMD 16, programmer 24, server 314, and computing devices 316A-316N may each comprise one or more processors, such as one or more microprocessors, DSPs, ASICs, FPGAs, programmable logic circuitry, or the like, that may perform various functions and operations, such as those described herein. For example, as illustrated in FIG. 14, server 314 may comprise one or more processors 315 and an input/output device 313, which need not be co-located.

Server 314 may, for example, monitor impedance, e.g., based measured impedance information received from IMD 16 and/or programmer 24 via network 312, to detect worsening heart failure of patient 14 using any of the techniques described herein. Server 314 may provide alerts relating to worsening heart failure of patient 16 via network 312 to patient 14 via access point 310, or to one or more clinicians via computing devices 316. In examples such as those described above in which IMD 16 and/or programmer 24 monitor the impedance, server 314 may receive an alert from the IMD or programmer via network 312, and provide alerts to one or more clinicians via computing devices 316. Server 314 may generate web-pages to provide alerts and information regarding the impedance, and may comprise a memory to store alerts and diagnostic or physiological parameter information for a plurality of patients.

Access point 310 may comprise a device that connects to network 312 via any of a variety of connections, such as telephone dial-up, digital subscriber line (DSL), or cable modem connections. In other examples, access point 310 may be coupled to network 312 through different forms of connections, including wired or wireless connections. Network 312 may comprise a local area network, wide area network, or global network, such as the Internet. System 300 may be implemented, in some aspects, with general network technology and functionality similar to that provided by the Medtronic CareLink® Network developed by Medtronic, Inc., of Minneapolis, Minn.

The techniques described in this disclosure, including those attributed to image IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various examples have been described. However, one of ordinary skill in the art will appreciate that various modifications may be made to the described examples without departing from the scope of the claims. For example, although described primarily with reference to intrathoracic impedance, in some examples other physiological parameters may be considered with intrathoracic impedance to detect worsening heart failure. Examples of other physiological parameters and techniques for detect worsening heart failure based on these parameters in combination with intrathoracic impedance are described in a commonly-assigned and co-pending application by Hettrick et al., entitled "USING MULTIPLE DIAGNOSTIC PARAMETERS FOR PREDICTING HEART FAILURE EVENTS," filed on even date herewith, and incorporated herein by reference in its entirety.

Furthermore, although described primarily with reference to examples that provide an alert in response to detecting worsening heart failure, other examples may additionally or alternatively automatically modify a therapy in response to detecting worsening heart failure in the patient. The therapy may be, as examples, a substance delivered by an implantable pump, cardiac resynchronization therapy, refractory period stimulation, or cardiac potentiation therapy. These and other examples are within the scope of the following claims.

The invention claimed is:

1. A method comprising:
periodically determining, using a medical device, an impedance of a patient based on measured impedances;
comparing each of the determined impedances to a respective reference impedance, wherein the respective reference impedance for each of the determined impedances is determined based on a plurality of previously determined impedances;
generating an index based on the comparisons between the determined impedances and the reference impedances;
determining a variability value based on the plurality of previously determined impedance values;
modifying the index over time based on the variability value and the comparisons between the determined impedances and the reference impedances;
comparing the index to at least one threshold; and
determining whether to provide an alert based on the comparison of the index to the at least one threshold.

2. The method of claim 1, wherein modifying the index based on the comparisons and the variability value comprises:
determining a modification based on one of the comparisons; and
reducing the modification based on the variability value.

3. The method of claim 2, wherein the variability value is scaled by a time dependent value that reduces an affect of the variability value on the modification over time.

4. The method of claim 3, wherein modifying an index over time based on the comparisons between the determined impedances and the reference impedances comprises: increasing the index by differences between the reference impedances and the determined impedances less the scaled variability value so long as the determined impedances are less than the reference impedances.

5. The method of claim 1, wherein determining the variability value comprises:
determining a plurality of absolute differences between successive ones of the previously determined impedances; and
determining a median of the differences as the variability value.

6. The method of claim 1, further comprising:
determining a value that increases as a function of time over which the index is greater than one of the thresholds; and
adding the value to the index when the index is greater than the threshold.

7. The method of claim 6, wherein adding the value to the index when the index is greater than the threshold comprises adding the value to the index when the index has been greater than the threshold for a threshold duration.

8. The method of claim 1, further comprising determining a subsequent one of the reference impedances based on a comparison of a current one of the determined impedances to a current one of the reference impedances, wherein determining the subsequent one of the reference impedances comprises:
increasing the current one of the reference impedances by a predetermined increment value if the current one of the determined impedances is greater than the current one of the reference impedances;
decreasing the current one of the reference impedances by a predetermined decrement value if the current one of the determined impedances is less than the current one of the reference impedances; and
varying at least one of the increment value or the decrement value over time to affect a slope of the index.

9. The method of claim 8, wherein varying at least one of the increment value or the decrement value over time comprises decreasing the at least one of the increment value or the decrement value over time.

10. The method of claim 8, wherein varying at least one of the increment value or the decrement value over time comprises varying the at least one of the increment value or the decrement value over a predetermined period of time from implantation of electrodes used to measure the impedance of the patient.

11. The method of claim 1,
wherein comparing each of the determined impedances to a respective reference impedance comprises determining differences between the reference impedances and the determined impedances,
wherein modifying an index over time based on the comparisons between the measured impedances and the reference impedances comprises determining the index as a sum of the previous X or fewer differences so long as the measured impedance is less than the reference impedance, and wherein X is a predetermined constant value.

12. The method of claim 1,
wherein comparing the index to at least one threshold comprises comparing the index to a first threshold and a second threshold,
wherein the first threshold is greater than the second threshold, and
wherein determining whether to provide an alert based on the comparison of the index to the at least one threshold comprises:
providing the alert when the index is at least one of greater than or equal to the first threshold, and
stopping the alert when the index is subsequently at least one of less than or equal to the second threshold.

13. The method of claim 1, wherein the alert indicates a possible heart failure decompensation event.

14. The method of claim 1, wherein the impedance comprises an intrathoracic impedance.

15. The method of claim 1, further comprising determining whether to provide an alert based on the comparison of the index to the at least one threshold using an implantable medical device.

16. A method comprising:
periodically determining, using a medical device, an impedance of a patient based on a plurality of measured impedances;
comparing each of the determined impedances to a respective reference impedance, wherein the respective reference impedance for each of the determined impedances is determined based on a plurality of previously determined impedances, and wherein comparing each of the determined impedances to a respective reference impedance comprises determining differences between the reference impedances and the determined impedances;
determining an index based on the previous X or fewer comparisons, wherein determining the index based on the previous X or fewer comparisons comprises determining the index as a sum of the previous X or fewer differences so long as the determined impedance is less than the reference impedance, and wherein X is a predetermined constant value;
comparing the index to at least one threshold; and
determining whether to provide an alert based on the comparison of the index to the at least one threshold, wherein determining the index as a sum of the previous X or fewer differences comprises:
storing the differences in a buffer with a limit of X differences; and
summing the index values stored in the buffer.

17. The method of claim 16, further comprising resetting the buffer when a current determined impedance is greater than a respective reference impedance value.

18. A method comprising:
periodically determining, using a medical device, an impedance of a patient based on a plurality of measured impedances;
comparing each of the determined impedances to a respective reference impedance, wherein the respective reference impedance for each of the determined impedances is determined based on a plurality of previously determined impedances;
modifying an index over time based on the comparisons between the determined impedances and the reference impedances;

comparing the index to a plurality of thresholds; and
determining whether to provide an alert based on the comparison of the index to the plurality of thresholds,
wherein comparing the index to a plurality of thresholds comprises comparing the index to a first threshold and a second threshold,
wherein the first threshold is greater than the second threshold, and
wherein determining whether to provide an alert based on the comparison of the index to the at least one threshold comprises:
providing the alert when the index is at least one of greater than or equal to the first threshold; and
stopping the alert when the index is subsequently at least one of less than or equal to the second threshold.

19. A system comprising:
a plurality of electrodes;
a medical device coupled to the electrodes that periodically measures an impedance of the patient; and
a processor that:
periodically determines an impedance value based on a plurality of the measured impedances,
compares each of the determined impedance values to a respective reference impedance, wherein the respective reference impedance for each of the determined impedance values is determined based on a plurality of previously determined impedance values,
generates an index based on the comparisons between the determined impedances and the reference impedances,
determines a variability value based on the plurality of previously determined impedance values,
modifies the index over time based on the variability value and the comparisons between the determined impedance values and the reference impedances,
compares the index to at least one threshold, and
determines whether to provide an alert based on the comparison of the index to the at least one threshold.

20. The system of claim 19, wherein the processor determines an index modification based on one of the comparisons, and reduces the modification based on the variability value.

21. The system of claim 20, wherein the processor scales the variability value by a time dependent value that reduces an affect of the variability value on the modification over time.

22. The system of claim 21, wherein the processor increases the index by differences between the reference impedances and the determined impedance values less the scaled variability value so long as the determined impedance values are less than the reference impedances.

23. The system of claim 19, wherein the processor determines a value that increases as a function of time over which the index is greater than one of the thresholds, and adds the value to the index when the index is greater than the threshold.

24. The system of claim 23, wherein the processor adds the value to the index when the index has been greater than the threshold for a threshold duration.

25. The system of claim 19,
wherein the processor determines a subsequent one of the reference impedances based on a comparison of a current one of the determined impedance values to a current one of the reference impedances, and
wherein the processor increases the current one of the reference impedances by a predetermined increment value if the current one of the determined impedance values is greater than the current one of the reference impedances, and decreases the current one of the reference impedances by a predetermined decrement value if the current one of the determined impedance values is less than the current one of the reference impedances, and varies at least one of the increment value or the decrement value over time.

26. The system of claim 25, wherein the processor decreases the at least one of the increment value or the decrement value over time.

27. The system of claim 25, wherein the processor varies the at least one of the increment value or the decrement value over a predetermined period of time from implantation of electrodes used to measure the impedance of the patient.

28. The system of claim 19, wherein the electrodes comprise a plurality of implantable electrodes, the medical device comprises an implantable medical device, and the processor comprises a processor of the implantable medical device.

29. The system of claim 28, wherein the implantable medical device comprises at least one of a pacemaker, a cardioverter, or a defibrillator.

30. A system comprising:
a plurality of electrodes;
a medical device coupled to the electrodes that periodically measures an impedance of a patient;
a memory; and
a processor that:
periodically determines an impedance value based on a plurality of the measured impedances;
compares each of the determined impedance values to a respective reference impedance to determine differences between the reference impedances and the determined impedance values, wherein the respective reference impedance for each of the determined impedance values is determined based on a plurality of previously determined impedance values;
determines an index as a sum of the previous X or fewer differences so long as the measured impedance is less than the reference impedance, wherein X is a predetermined constant value;
compares the index to at least one threshold; and
determines whether to provide an alert based on the comparison of the index to the at least one threshold, wherein the processor stores the differences in a buffer with a limit of X differences in the memory and sums the index values stored in the buffer.

31. The system of claim 30, wherein the processor resets the buffer when a current measured impedance is greater than a respective reference impedance value.

32. A system comprising:
a plurality of electrodes;
a medical device coupled to the electrodes that periodically measures an impedance of a patient; and
a processor that:
periodically determines an impedance value based on a plurality of the measured impedances,
compares each of the determined impedance values to a respective reference impedance, wherein the respective reference impedance for each of the determined impedance values is determined based on a plurality of previous measured impedances;
modifies an index over time based on the comparisons between the determined impedance values and the reference impedances;
compares the index to a plurality of thresholds; and
determines whether to provide an alert based on the comparison of the index to the plurality of thresholds, wherein the processor compares the index to a first threshold and a second threshold, wherein the first threshold is greater than the second threshold, and wherein the processor provides the alert when the index is at least one of greater than or equal to the first threshold, and stops the alert when the index is subsequently at least one of less than or equal to the second threshold.

33. A system comprising:
means for periodically determining an impedance of a patient based on a plurality of measured impedances;
means for comparing each of the determined impedances to a respective reference impedance, wherein the respective reference impedance for each of the determined impedances is determined based on a plurality of previous measured impedances;
means for generating an index based on the comparisons between the determined impedances and the reference impedances;
means for determining a variability value based on the plurality of previously determined impedance values;
means for modifying the index over time based on the variability value and the comparisons between the determined impedances and the reference impedances;
means for comparing the index to at least one threshold; and
means for determining whether to provide an alert based on the comparison of the index to the at least one threshold.

* * * * *